(12) United States Patent
Yamaha

(10) Patent No.: US 11,458,217 B2
(45) Date of Patent: Oct. 4, 2022

(54) ULTRAVIOLET-EMITTING DEVICE

(71) Applicant: ASAHI KASEI KABUSHIKI KAISHA, Tokyo (JP)

(72) Inventor: Yoshiro Yamaha, Tokyo (JP)

(73) Assignee: Asahi Kasei Kabushiki Kaisha, Tokyo (JP)

( * ) Notice: Subject to any disclaimer, the term of this patent is extended or adjusted under 35 U.S.C. 154(b) by 328 days.

(21) Appl. No.: 16/628,270

(22) PCT Filed: Jul. 4, 2018

(86) PCT No.: PCT/JP2018/025414
§ 371 (c)(1),
(2) Date: Jan. 3, 2020

(87) PCT Pub. No.: WO2019/009343
PCT Pub. Date: Jan. 10, 2019

(65) Prior Publication Data
US 2020/0155718 A1     May 21, 2020

(30) Foreign Application Priority Data

Jul. 4, 2017 (JP) .............................. JP2017-131132
Apr. 20, 2018 (JP) .............................. JP2018-081734

(51) Int. Cl.
*A61L 2/10* (2006.01)
*H05B 45/18* (2020.01)
(Continued)

(52) U.S. Cl.
CPC .............. *A61L 2/10* (2013.01); *H01L 31/153* (2013.01); *H01L 33/505* (2013.01);
(Continued)

(58) Field of Classification Search
None
See application file for complete search history.

(56) References Cited

U.S. PATENT DOCUMENTS 5,635,109 A     6/1997 Otsuka
5,961,883 A    10/1999 Yamazaki et al.
(Continued)

FOREIGN PATENT DOCUMENTS

CN     101278407 B  * 11/2010 ......... H01L 31/0322
EP       1926154 A2    5/2008
(Continued)

OTHER PUBLICATIONS

International Search Report (with partial translation) and Written Opinion dated Oct. 9, 2018, issued in corresponding International Patent Application No. PCT/JP2018/025414.
(Continued)

*Primary Examiner* — Andrew Smyth
(74) *Attorney, Agent, or Firm* — Morgan, Lewis & Bockius LLP

(57) ABSTRACT

The object of the present invention is to provide an ultraviolet-emitting device which achieves suppresses deterioration, and prolonged life of the components used in a light-emitting device while monitoring a light emitting state of the light-emitting element and maintaining an emission intensity. The ultraviolet-emitting device is provided with a light-emitting element configured to emit an ultraviolet ray, a mounting board on which the light-emitting element is placed, and a fluorescent glass element placed at a position irradiated with the ultraviolet ray emitted by the light-emitting element, and placed in a through hole formed through the mounting board, emitting fluorescence in a visible range by excitation of an ultraviolet ray.

20 Claims, 11 Drawing Sheets

(51) Int. Cl.
  *H05B 45/12* (2020.01)
  *H01L 31/153* (2006.01)
  *H01L 33/50* (2010.01)
  *H01L 33/60* (2010.01)

(52) U.S. Cl.
  CPC ............ *H01L 33/507* (2013.01); *H01L 33/60* (2013.01); *H05B 45/12* (2020.01); *H05B 45/18* (2020.01); *A61L 2202/11* (2013.01)

(56) References Cited

U.S. PATENT DOCUMENTS

| | | |
|---|---|---|
| 6,335,529 B1 | 1/2002 | Sekii et al. |
| 2014/0209928 A1 | 7/2014 | Teng et al. |
| 2018/0294294 A1 | 10/2018 | Kim et al. |
| 2019/0070577 A1 | 3/2019 | Taguchi |
| 2019/0113219 A1* | 4/2019 | Niemiec ................ A01M 1/08 |

FOREIGN PATENT DOCUMENTS

| | | | | |
|---|---|---|---|---|
| JP | H08-133780 A | | 5/1996 | |
| JP | H10-167755 A | | 6/1998 | |
| JP | 2001-339286 A | | 12/2001 | |
| JP | 2005-227241 A | | 8/2005 | |
| JP | 2005-268262 A | | 9/2005 | |
| JP | 2007-027295 A | | 2/2007 | |
| JP | 4087113 B2 | * | 5/2008 | ........... C03C 23/002 |
| JP | 2008-153014 A | | 7/2008 | |
| JP | 2008153014 A | * | 7/2008 | |
| JP | 2009-080078 A | | 4/2009 | |
| JP | 2009-255038 A | | 11/2009 | |
| JP | 2010-082589 A | | 4/2010 | |
| JP | 2010082589 A | * | 4/2010 | |
| JP | 2010-205860 A | | 9/2010 | |
| JP | 2010-257867 A | | 11/2010 | |
| JP | 2012-018077 A | | 1/2012 | |
| JP | 2014-049611 A | | 3/2014 | |
| JP | 2014-233383 A | | 12/2014 | |
| KR | 20130119726 A | * | 11/2013 | |
| WO | 2000/011440 A1 | | 3/2000 | |
| WO | 2017078201 A1 | | 1/2015 | |
| WO | 2017/073776 A1 | | 5/2017 | |

OTHER PUBLICATIONS

Communication Pursuant to Article 94(3) EPC corresponding to European Patent Application No. 18827929.3-1211, dated Jul. 17, 2020, 10 pages.

Supplementary European Search Report, issued in corresponding International Patent Application No. 18827929.3, dated Mar. 30, 2020, 4 pages.

International Preliminary Report on Patentability dated Oct. 16 Jan. 2018, issued in Corresponding International Patent Application No. PCT/JP2018/025414.

* cited by examiner

ULTRAVIOLET-EMITTING DEVICE

TECHNICAL FIELD

The present invention relates to an ultraviolet-emitting device which adjusts a light-emitting element emitting light having wavelengths shorter than the visible range.

BACKGROUND ART

A glass dosimeter reader is known to read the dose of radiation applied to a fluorescent glass element emitting fluorescence in the visible range by excitation of ultraviolet rays, using the characteristics of the fluorescent glass element (for example, patent literature 1).

An adjustment device is also known to detect a certain component of ultraviolet rays emitted by a light-emitting element and adjust the emission intensity (for example, patent literature 2).

CITATION LIST

Patent Literature

PTL 1: JP 2012-18077 A
PTL 2: JP 2007-27295 A

SUMMARY OF INVENTION

Technical Problem

It is an object of the present invention to provide an ultraviolet-emitting device which achieves suppresses deterioration, and prolonged life of the components used in a light-emitting device while monitoring a light emitting state of the light-emitting element and maintaining an emission intensity.

In order to achieve the object, an ultraviolet-emitting device according to one aspect of the present invention is provided with a light-emitting element configured to emit an ultraviolet ray, a board on which the light-emitting element is placed, a fluorescent glass element placed at a position irradiated with the ultraviolet ray emitted by the light-emitting element, and placed in a through hole formed through the board, emitting fluorescence in a visible range by excitation of an ultraviolet ray, and a photodetection element configured to detect an intensity of the fluorescence emitted by the fluorescent glass element.

In order to achieve the object, an ultraviolet-emitting device according to another aspect of the present invention is provided with a light-emitting element configured to emit an ultraviolet ray, a fluorescent glass element which is placed at a position, irradiated with the ultraviolet ray emitted by the light-emitting element, protruding higher than the light-emitting element, and emitting fluorescence in a visible range by excitation of an ultraviolet ray, a board on which the light-emitting element is placed, and a photodetection element configured to detect an intensity of the fluorescence emitted by the fluorescent glass element.

According to each aspect of the present invention, it is possible to achieve suppresses deterioration, and prolonged life of the components used in a light-emitting device while monitoring a light emitting state of the light-emitting element and maintaining an emission intensity.

BRIEF DESCRIPTION OF DRAWINGS

FIG. 11 illustrates diagrams for explaining an ultraviolet-emitting device 4 according to Embodiment 2-3 of the present invention, in which

FIG. 12 illustrates diagrams for explaining an ultraviolet-emitting device according to modifications to Embodiments 1 and 2 of the present invention, in which

DESCRIPTION OF EMBODIMENTS

Embodiment 1

An ultraviolet-emitting device according to Embodiment 1 of the present invention will be described below with reference to FIGS. 1 to 7. The schematic configuration of an ultraviolet-emitting device 1 according to the present embodiment will be described first with reference to FIGS. 1 to 4.

Figure 1:
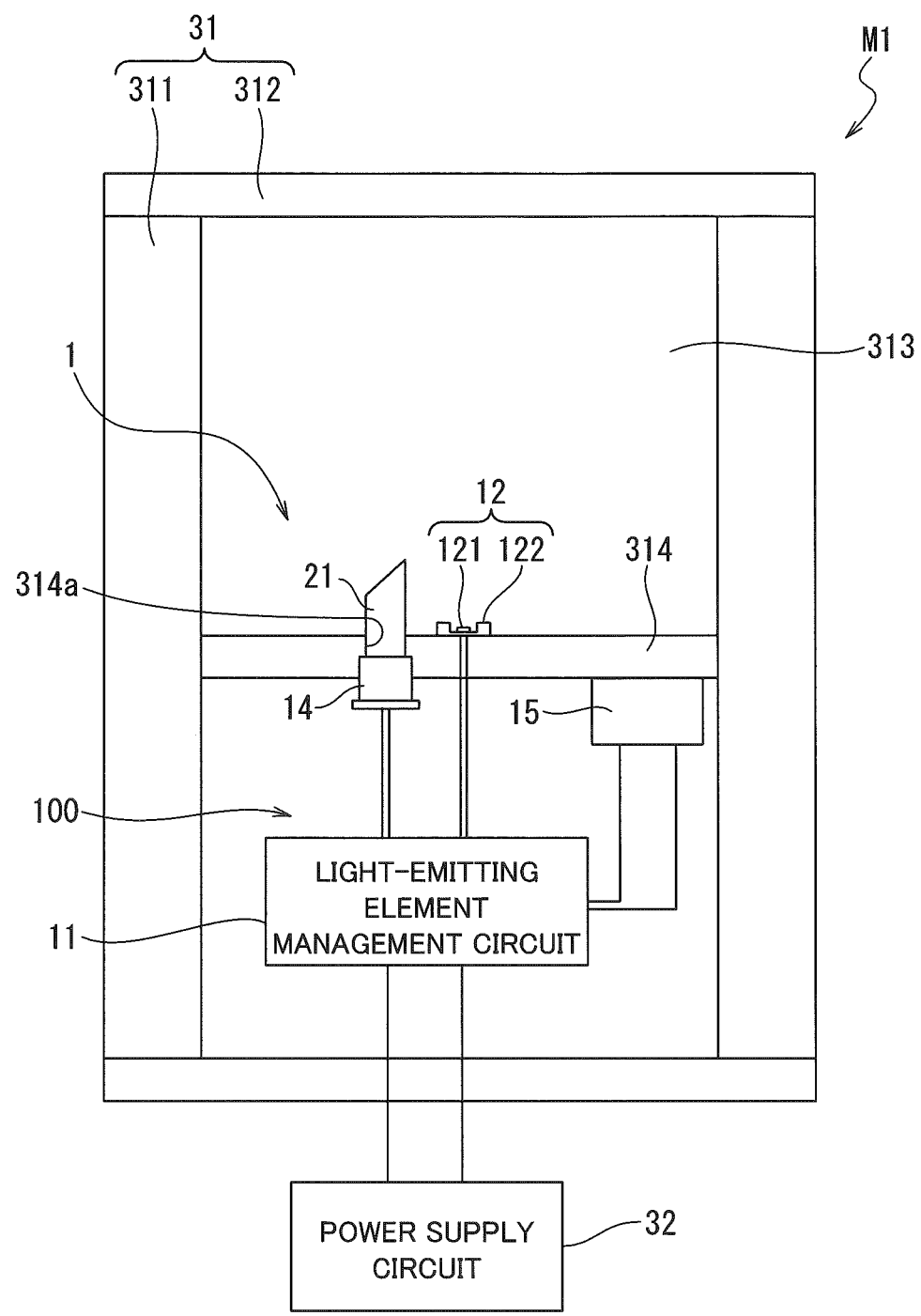
FIG. 1 is a diagram typically illustrating the schematic configuration of a sterilization module M1 including an ultraviolet-emitting device 1 according to Embodiment 1 of the present invention.

As illustrated in FIG. 1, the ultraviolet-emitting device 1 according to the present embodiment includes a light-emitting element 121 which emits ultraviolet rays, a mounting board (an example of a board) 314 on which the light-emitting element 121 is placed, and a fluorescent glass element 21 which is placed at a position irradiated with the ultraviolet rays emitted by the light-emitting element 121 and emits fluorescence in the visible range by excitation of the ultraviolet rays. The light-emitting element 121 is provided in a ceramic package 122 including a ceramic board. The light-emitting element 121 is mounted on the ceramic board. The light-emitting element 121 and the ceramic package 122 are provided in a light source 12. The ultraviolet-emitting device 1 includes a photodetection element 14 which detects the intensity of the fluorescence emitted by the fluorescent glass element 21, and a light-emitting element management circuit (an example of a management circuit) 11 which controls the light-emitting element 121, based on the intensity of the fluorescence detected by the photodetection element 14.

The ultraviolet-emitting device 1 includes an electronic component group 100. The electronic component group 100 may include at least one of a photodetection element 14 which detects at least one of the presence or the absence of the emission and emission intensity (fluorescence intensity) of light emitted by the fluorescent glass element 21, a light-emitting element management circuit 11 which adjusts at least one of the presence or the absence of the emission and emission intensity of ultraviolet rays emitted by the light-emitting element 121, and a temperature sensor 15 (to be described in detail later). In the ultraviolet-emitting device 1 according to the present embodiment, the electronic component group 100 includes the photodetection element 14, the light-emitting element management circuit 11, and the temperature sensor 15. The light-emitting element management circuit 11 is configured to control the light-emitting element 121, based on the fluorescence intensity detected by the photodetection element 14. The photodetection element 14, the light-emitting element management circuit 11, and the temperature sensor 15 correspond to examples of electronic components. In this manner, the electronic component group 100 includes a plurality of electronic components. In other words, a plurality of electronic components are provided in the ultraviolet-emitting device 1 to form the electronic component group 100.

The ultraviolet-emitting device 1 is accommodated in a box-shaped or cylindrical sterilization module M1. The sterilization module M1 includes an accommodation member 31 which can accommodate an object (not illustrated) to be sterilized by the ultraviolet-emitting device 1 and the light-emitting element 121 in an external light-shielded state. The sterilization module M1 includes an accommodation space 313 which can accommodate the ultraviolet-emitting device 1 and the object to be sterilized. The sterilization module M1 is configured to sterilize running water (an example of an object to be sterilized) flowing from one outside into the accommodation space 313, using ultraviolet rays emitted by the light-emitting element 121, and guide the sterilized running water to the other outside.

The accommodation member 31 has a main body portion 311 having the accommodation space 313, and a lid portion 312 which can block incidence of external light on the accommodation space 313. The main body portion 311 has a box shape open at its one end. The lid portion 312 is provided on the main body portion 311 to allow opening and closing of one end of the main body portion 311. The sterilization module M1 has its lid portion 312 opened to open one end of the main body portion 311, and, after the ultraviolet-emitting device 1 is accommodated in the accommodation space 313, has its lid portion 312 closed to form a closed space in the accommodation space 313. After a closed space is formed in the accommodation space 313, running water flows into the sterilization module M1.

The sterilization module M1 has in the accommodation space 313, a mounting board 314 on which the light source 12 and the like is placed. The mounting board 314 supports not only the light source 12 but also the fluorescent glass element 21, the photodetection element 14, and the temperature sensor 15 mounted on it. A through hole 314a having a stepped wall surface is formed in the mounting substrate 314. The fluorescent glass element 21 and the photodetection element 14 are inserted into the through hole 314a. If there is a gap between the fluorescent glass element 21 and the through hole 314a in a direction perpendicular to the through direction of the through hole 314a, light emitted from the fluorescent glass element 21 leaks out of the gap. As a result, the amount of light detected by the photodetection element 14 is reduced, so that the detection accuracy is lowered. For this reason, the fluorescent glass element 21 is good to be inserted in a state where the outer surface is in contact with the inner wall surface of the through hole 314a. This prevents light emitted from the fluorescent glass element 21 from leaking between the fluorescent glass element 21 and the through hole 314a, thereby suppressing a decrease in the amount of light detected by the photodetection element 14, and the detection accuracy is improved. In addition, when the outer surface of the fluorescent glass element 21 and the inner wall surface of the through hole 314a are not in contact with each other, the gap between the fluorescent glass element 21 and the through hole 314a in the direction orthogonal to the through direction of the through hole 314a is preferably as small as possible from the viewpoint of improving the fluorescence detection accuracy of the photodetection element 14. The fluorescent glass element 21 and the photodetection element 14 are arranged to face each other in the through hole 314a. The mounting board 314 is made of a material (for example, aluminum) having a low thermal resistance and therefore also serves as a heat radiation member for dissipating heat generated by the light-emitting element 121. The sterilization module M1 also includes a power supply circuit 32 which supplies power to the ultraviolet-emitting device 1 and the like. The power supply circuit 32 is connected to a power supply cable connected to the ultraviolet-emitting device 1 and routed out of the accommodation member 31.

Figure 2:
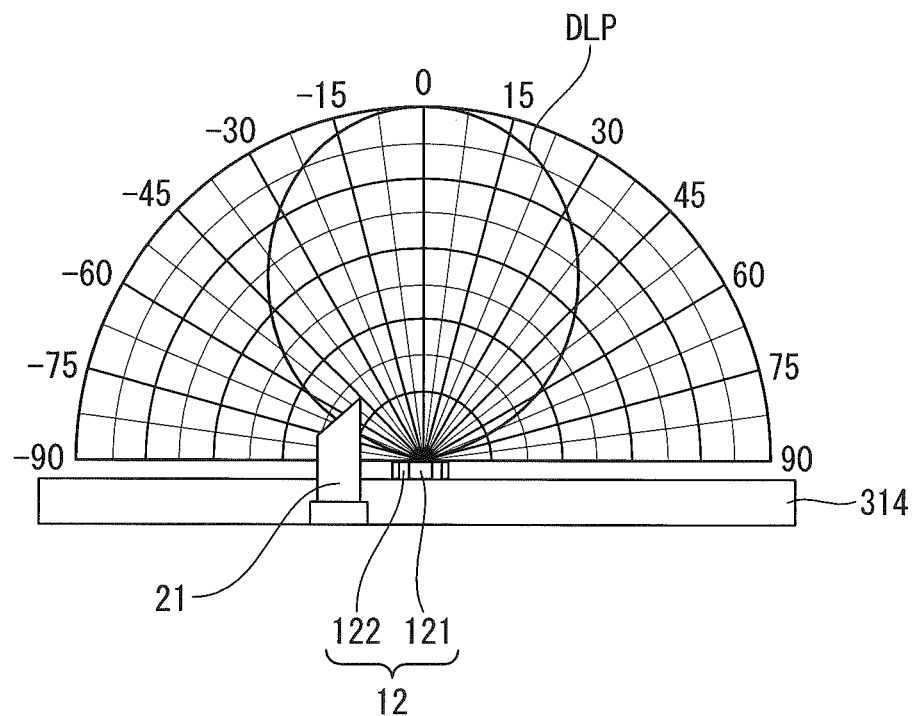
FIG. 2 is a diagram for explaining the relationship between a fluorescent glass element 21 and the directivity of ultraviolet rays emitted by a light-emitting element 121 provided in the ultraviolet-emitting device 1 according to Embodiment 1 of the present invention.
Figure 3:
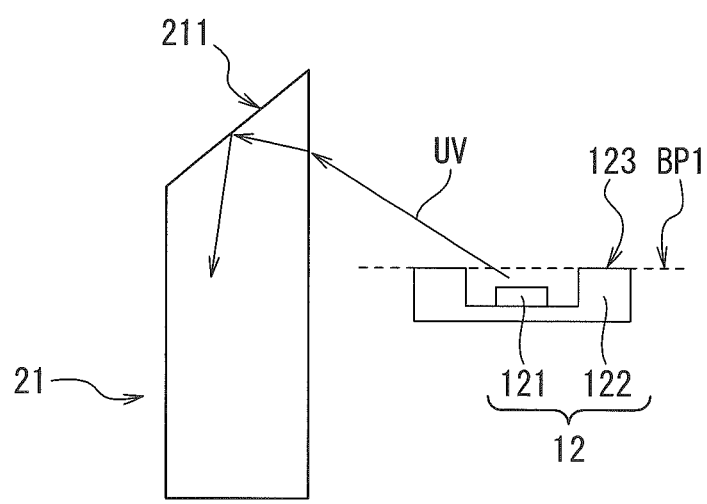
FIG. 3 is a diagram illustrating an exemplary shape of the fluorescent glass element 21 provided in the ultraviolet-emitting device 1 according to Embodiment 1 of the present invention.

The fluorescent glass element 21 will be described below with reference to FIGS. 2 and 3 in conjunction with FIG. 1. FIG. 2 illustrates only the light source 12, the fluorescent glass element 21, and the mounting board 314 of the components provided in the accommodation space 313 of the sterilization module M1, to facilitate an understanding. FIG. 2 also illustrates an exemplary light distribution pattern of the light-emitting element 121, to facilitate an understanding. FIG. 3 illustrates only the fluorescent glass element 21 and the light source 12 of the components illustrated in FIG. 2, to facilitate an understanding.

As illustrated in FIG. 2, the fluorescent glass element 21 is placed adjacent to the light-emitting element 121 to protrude higher than the light-emitting element 121. More specifically, the fluorescent glass element 21 protrude higher than the light-emitting element 121 with respect to an upper surface 123 of the ceramic package 122 accommodating the light-emitting element 121 and is adjacent to the light-emitting element 121 or adjacent to the light source 12. The "upper surface" may be defined herein, for example, as the surface of the ceramic package 122 opposite to a surface where the ceramic package 122 comes into contact with the mounting board 314, or as a virtual plane BP1 (see FIG. 3) including the surface. In this case, the height plane defining the light distribution pattern DLP is the virtual plane BP1. The light-emitting element 121 emits ultraviolet rays having a distribution of luminous intensity similar to the Lambert distribution of luminous intensity, as indicated by a light distribution pattern DLP. The light distribution pattern DLP possesses a directivity having a half-power angle of about 50°. By placing the fluorescent glass element 21 adjacent to the light-emitting element 121 to protrude higher than the light-emitting element 121, the fluorescent glass element 21 is partially included in the region irradiated with ultraviolet rays by the light-emitting element 121. The ultraviolet-emitting device 1 is not placed on the optical axis of the ultraviolet rays emitted by the light-emitting element 121 but crosses the ultraviolet rays at a position where the ultraviolet rays emitted by the light-emitting element 121 have a relatively low intensity. The ultraviolet-emitting device 1 can guide the ultraviolet rays emitted by the light-emitting element 121 to the fluorescent glass element 21 while suppressing attenuation of the ultraviolet rays impinging on the object to be sterilized. Hence, the sterilization module M1 can detect the effective light emission intensity while preventing a decrease in sterilization efficiency of the object to be sterilized.

The fluorescent glass element 21 exhibits a fluorescence spectrum having a maximum peak in a wavelength range in which the photodetection element 14 has a relatively high detection sensitivity. The fluorescent glass element 21 exhibits a fluorescence spectrum having a maximum peak at a wavelength of, for example, 540 nm and is configured to emit green fluorescence. The photodetection element 14 exhibits a maximum sensitivity at a wavelength of, for example, 560 nm and detection characteristics having a full width at half maximum of about 120 nm. Hence, the photodetection element 14 can receive light emitted by the fluorescent glass element 21 even when ultraviolet rays are applied to the fluorescent glass element 21 in a small amount and the fluorescent glass element 21 emits low-intensity fluorescence.

The fluorescent glass element 21 is formed in a pillar shape and has, at its one end, an inclined surface lower in the direction away from the light-emitting element 121, as illustrated in FIG. 3. More specifically, the fluorescent glass element 21 has, at its one end, an inclined surface 211 whose level with reference to the upper surface 123 of the ceramic package 122 is lower in the direction away from the light-emitting element 121. The inclined surface 211 is inclined at an angle which allows total reflection of ultraviolet rays UV incident on the fluorescent glass element 21. When, for example, the fluorescent glass element 21 is made of an ultraviolet-transmissible material, the ultraviolet rays UV incident on the fluorescent glass element 21 can be totally reflected by the inclined surface 211. Hence, the amount of ultraviolet rays exciting the fluorescent glass element 21 increases, and the intensity of fluorescence emitted by the fluorescent glass element 21, in turn, increases. This improves the detection sensitivity of the photodetection element 14.

The fluorescent glass element 21 has, for example, a quadrangular prismatic shape, as illustrated in FIGS. 2 and 3. The shape of the fluorescent glass element 21 is not limited to this and may be prismatic shapes other than a quadrangular prismatic shape, circular and elliptical shapes and the like. The fluorescent glass element 21 may have no inclined surface 211. The fluorescent glass element 21 may be mounted on the mounting board 314 as inclined at an angle which allows total reflection of the ultraviolet rays incident on the fluorescent glass element 21 by one end of the fluorescent glass element 21.

The circuit configuration of the ultraviolet-emitting device 1 will be described below with reference to FIG. 4.

Figure 4:
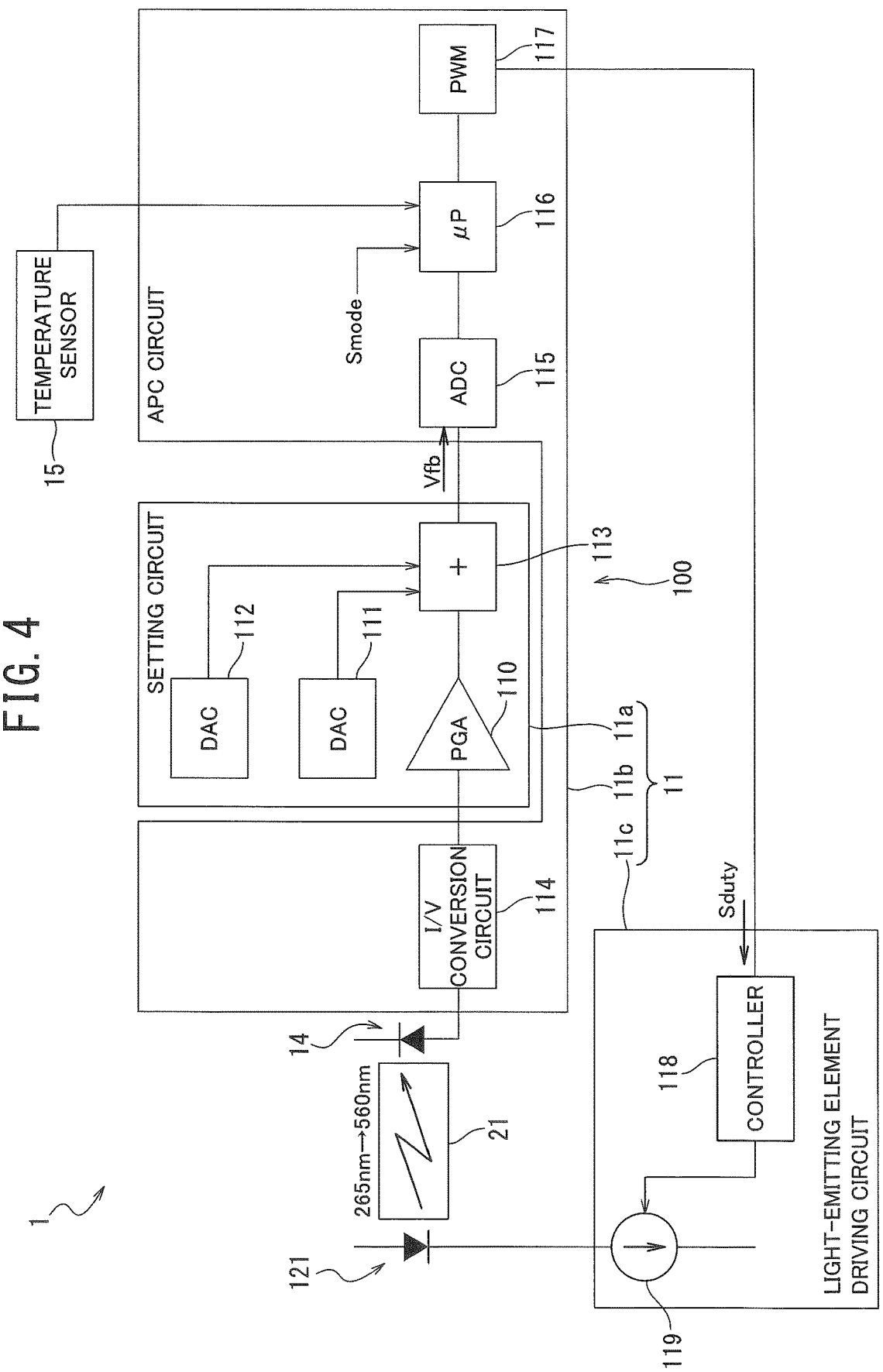
FIG. 4 is a circuit block diagram illustrating the schematic configuration of the ultraviolet-emitting device 1 according to Embodiment 1 of the present invention.

The ultraviolet-emitting device 1 includes a light-emitting element 121, a fluorescent glass element 21, a photodetection element 14, and a light-emitting element management circuit 11, as illustrated in FIG. 4.

The light-emitting element 121 is designed as, for example, an LED (Light Emitting Diode) which emits ultraviolet rays. The anode of the light-emitting element 121 is connected to, for example, an analog power supply and the cathode of the light-emitting element 121 is connected to, for example, the positive electrode of a constant current source 119 (to be described in detail later) provided in a light-emitting element driving circuit 11c.

The fluorescent glass element 21 emits, for example, green fluorescence (having a wavelength of, for example, 560 nm) upon being excited by ultraviolet rays (having a wavelength of, for example, 265 nm) emitted by the light-emitting element 121, as described above. In other words, the fluorescent glass element 21 converts 265-nm-wavelength light into 560-nm-wavelength light.

The photodetection element 14 is designed as, for example, a PD (Photodiode). The cathode of the photodetection element 14 is connected to, for example, an analog power supply and its anode connected to, for example, a current-to-voltage conversion circuit 114 (to be described in detail later) provided in an auto power control circuit 11b. The photodetection element 14 is configured to convert the fluorescence emitted by the fluorescent glass element 21 into a current and output it to the current-to-voltage conversion circuit 114.

The light-emitting element management circuit 11 has a setting circuit (an example of a setting unit) 11a which sets a target value for causing the light-emitting element 121 to emit light with a desired emission intensity, and an APC (Auto Power Control) circuit (an example of an automatic power controller) 11b which maintains the light-emitting element 121 at the desired emission intensity, as illustrated in FIG. 4. The target value set by the setting circuit 11a is the value of the drive current for the light-emitting element 121, although details will be described later. The light-emitting element management circuit 11 further has a light-emitting element driving circuit (an example of a driver) which drives the light-emitting element 121.

The setting circuit 11a has an amplifier 110 which amplifies a voltage based on a detection signal obtained by the photodetection element 14, a bias adjuster 111 which adjusts the DC bias of the voltage output from the amplifier 110, and an offset adjuster 112 which adjusts an offset voltage included in the voltage output from the amplifier 110. The setting circuit 11a further has an addition unit 113 which sums the voltage output from the amplifier 110, that output from the bias adjuster 111, and that output from the offset adjuster 112.

The input terminal of the amplifier 110 is connected to the output terminal of the current-to-voltage conversion circuit 114 provided in the auto power control circuit 11b. The output terminal of the amplifier 110 is connected to one of the three input terminals of the addition unit 113. The one remaining terminal of the addition unit 113 is connected to the output terminal of the bias adjuster 111 and the other remaining terminal of the addition unit 113 is connected to the output terminal of the offset adjuster 112. The output terminal of the addition unit 113 is connected to the input terminal of an analog-to-digital converter 115 (to be described in detail later) provided in the auto power control circuit 11b. The input terminal of the bias adjuster 111, to receive an input bit signal, is connected to a predetermined output terminal of a microprocessor 116 (to be described in detail later) provided in the auto power control circuit 11b. The input terminal of the offset adjuster 112, to receive an input bit signal, is connected to a predetermined output terminal of the microprocessor 116.

The amplifier 110 is designed as, for example, a PGA (Programmable Gain Amplifier). The amplifier 110 is configured to amplify a voltage input from the current-to-voltage conversion circuit 114 and output it to the addition unit 113. The amplification factor (gain) of the amplifier 110 is adjusted as needed upon setting of a target drive current for causing the light-emitting element 121 to emit light with a desired emission intensity (to be sometimes simply referred to as "a target drive current for the light-emitting element 121" hereinafter) and at the start of the operation of the light-emitting element 121, although details will be described later.

The bias adjuster 111 is designed as, for example, a digital-to-analog conversion circuit (Digital-to-Analog Converter: DAC). In the present embodiment, the bias adjuster 111 includes a DAC for high-order 8 bits and a DAC for low-order 8 bits. The bias adjuster 111 allows bias adjustment of the voltage output from the amplifier 110, using 16 bits accordingly. Hence, the bias adjuster 111 allows bias adjustment with a sufficient resolution even when a small amount of light is detected by the photodetection element 14. The number of input bits of the bias adjuster 111 is not limited to 16 bits and may be set as appropriate in accordance with the amount of light detected by the photodetection element 14. The voltage output from the bias adjuster 111 (that is, the input bit value) is adjusted as needed at the start of the operation of the light-emitting element 121, although details will be described later.

The offset adjuster 112 is designed as, for example, a digital-to-analog conversion circuit (Digital-to-Analog Converter: DAC). In the present embodiment, the offset adjuster 112 includes a DAC for high-order 8 bits and a DAC for low-order 8 bits. The offset adjuster 112 allows offset adjustment of the voltage output from the amplifier 110, using 16 bits accordingly. Hence, the offset adjuster 112 allows offset adjustment with a sufficient resolution even when a small amount of light is detected by the photodetection element 14. The number of input bits of the offset adjuster 112 is not limited to 16 bits and may be set as appropriate in accordance with the amount of light detected by the photodetection element 14. The offset adjuster 112 is used to adjust an offset voltage generated by the entire circuit constituting the ultraviolet-emitting device 1. The voltage output from the offset adjuster 112 (that is, the input bit value) is adjusted as needed upon setting of a target drive current for the light-emitting element 121, although details will be described later.

The addition unit 113 is configured to output to the auto power control circuit 11b, a sum voltage obtained by summing the voltage output from the amplifier 110, the voltage output from the bias adjuster 111, and the voltage output from the offset adjuster 112. In other words, the addition unit 113 has a 3-input/1-output configuration. The addition unit 113 can have various circuit configurations. For example, the addition unit 113 may have two 2-input/1-output operational amplifiers, one of which is configured to sum the voltage output from the bias adjuster 111 and the voltage output from the offset adjuster 112 and the other of which is configured to sum the voltage output from the former operational amplifier and the voltage output from the amplifier 110. Upon setting of a target drive current for the light-emitting element 121, the addition unit 113 finally outputs a voltage based on the emission intensity of the light-emitting element 121 driven by the target drive current as a feedback voltage Vfb. The addition unit 113 further outputs a voltage based on the emission intensity of the light-emitting element 121 as a feedback voltage Vfb during a sterilization operation for the object to be sterilized by the light-emitting element 121.

The auto power control circuit 11b has a current-to-voltage (to be sometimes referred to as "I/V" hereinafter) conversion circuit 114 having its input terminal connected to the anode of the photodetection element 14, as illustrated in FIG. 4. The I/V conversion circuit 114 is implemented using, for example, a current input operational amplifier, although a detailed circuit configuration will not be described. The output terminal of the I/V conversion circuit 114 is connected to the noninverting input terminal of the amplifier 110 provided in the setting circuit 11a. The I/V conversion circuit 114 is configured to convert a current input from the photodetection element 14 into a voltage and output it to the amplifier 110.

The auto power control circuit 11b has an analog-to-digital converter ("analog-to-digital" will sometimes be abbreviated as "A/D" hereinafter) 115 which converts an analog signal output from the setting circuit 11a into a digital signal. The auto power control circuit 11b also has a microprocessor (an example of a determination unit) 116 which determines whether the light-emitting element 121 maintains a desired emission intensity, based on the digital signal converted by the A/D converter 115. The auto power control circuit 11b further has a pulse-width modulated signal generator (an example of a generator) 117 which generates a PWM (Pulse Width Modulation) signal (an example of a control signal) for controlling the light-emitting element driving circuit (an example of a driver) 11c, based on an instruction from the microprocessor 116. Referring to FIG. 4, the microprocessor is symbolized by "μP." Pulse width modulation will sometimes be abbreviated as "PWM" hereinafter. The auto power control circuit 11b determines whether the light-emitting element 121 operates with a desired emission intensity, based on the feedback voltage Vfb during a sterilization operation, although details will be described later.

The output terminal of the A/D converter 115 is connected to a predetermined input terminal, to receive a bit signal, of the microprocessor 116. The predetermined output terminal of the microprocessor 116 is connected to the input terminal of the PWM signal generator 117. The output terminal of the PWM signal generator 117 is connected to the input terminal of a controller 118 (to be described in detail later) provided in the light-emitting element driving circuit 11c.

The A/D converter (Analog-to-Digital Converter: ADC) 115 converts the feedback voltage Vfb of an analog signal input from the addition unit 113 provided in the setting circuit 11a into a digital signal and outputs it to the microprocessor 116.

The microprocessor 116 stores a digital signal, input from the A/D converter 115 when setting of a target drive current for the light-emitting element 121 is complete, in a predetermined storage area as a target code. The target code is the condition of a drive current for driving the light-emitting element 121 with a desired emission intensity. After storing a target code, the microprocessor 116 stores the allowable operating range of the light-emitting element 121 in a predetermined storage area as a threshold code. The microprocessor 116 sets an upper limit threshold code defining the upper limit and a lower limit threshold code defining the lower limit of the allowable operating range of the light-emitting element 121.

The microprocessor 116 compares the digital signal input from the A/D converter 115 with the target code and the threshold code during a sterilization operation for the object to be sterilized by the light-emitting element 121. When the value of the input digital signal falls within the range between the target code and the threshold code, the microprocessor 116 determines that the light-emitting element 121 maintains a desired emission intensity. When the value of the input digital signal falls outside the range between the target code and the threshold code, the microprocessor 116 determines that the light-emitting element 121 maintains no desired emission intensity. The microprocessor 116 outputs no special instruction signal to the PWM signal generator 117 when it determines that the light-emitting element 121 maintains a desired emission intensity. The microprocessor 116 outputs a signal for instructing the PWM signal generator 117 to change the drive current when it determines that the light-emitting element 121 maintains no desired emission intensity. When the value of the input digital signal is larger than the upper limit threshold code, the microprocessor 116 outputs a signal for an instruction to decrease the amount of drive current to the PWM signal generator 117. When the value of the input digital signal is smaller than the lower limit threshold code, the microprocessor 116 outputs a signal for an instruction to increase the amount of drive current to the PWM signal generator 117. In this manner, the ultraviolet-emitting device 1 performs control to allow the light-emitting element 121 to maintain a desired emission intensity by feeding back the emission intensity of the light-emitting element 121 during a sterilization operation for the object to be sterilized by the light-emitting element 121.

The microprocessor 116 receives a state identification signal Smode, as illustrated in FIG. 4. The state identification signal Smode is used to identify whether the operation state of the ultraviolet-emitting device 1 is the state of a sterilization operation for the object to be sterilized by the light-emitting element 121 or the setting state of a target drive current for the light-emitting element 121. When the state identification signal Smode is "0," the microprocessor 116 determines that, for example, the state of a sterilization operation for the object to be sterilized by the light-emitting element 121 has been set. When the state identification signal Smode is "1," the microprocessor 116 determines that, for example, the setting state of a target drive current for the light-emitting element 121 has been set.

In other words, the microprocessor 116 can determine whether the light-emitting element 121 is active, based on the signal level of the state identification signal Smode. Therefore, when the light-emitting element management circuit 11 determines that external light has entered the accommodation member 31 that can accommodate the object to be sterilized and the light-emitting element 121, during the operation of the light-emitting element 121 while the object to be sterilized is ready to be sterilized, it stops the operation of the light-emitting element 121. When the sterilization module M1 is used in an unusual manner in the state of a sterilization operation for the object to be sterilized by the light-emitting element 121, the light-emitting element management circuit 11 immediately stops the light-emitting element 121, based on the state identification signal Smode. Hence, the ultraviolet-emitting device 1 can prevent ultraviolet rays from leaking out while the sterilization module M1 sterilizes the object to be sterilized.

The PWM signal generator 117 outputs a duty signal Sduty to the light-emitting element driving circuit 11c, based on the instruction signal input from the microprocessor 116. When a signal for an instruction to decrease the drive current is input from the microprocessor 116, the PWM signal generator 117 outputs a duty signal Sduty lower in duty ratio than the last output duty signal Sduty to the light-emitting element driving circuit 11c. When a signal for an instruction to increase the drive current is input from the microprocessor 116, the PWM signal generator 117 outputs a duty signal Sduty higher in duty ratio than the last output duty signal Sduty to the light-emitting element driving circuit 11c.

The ultraviolet-emitting device 1 includes a temperature sensor (an example of a temperature detector) 15 which detects the temperature of the light-emitting element 121. The auto power control circuit 11b controls the light-emitting element driving circuit 11c, based on the temperature detected by the temperature sensor 15. The output terminal of the temperature sensor 15 is connected to a predetermined input terminal of the microprocessor 116.

The temperature sensor 15 has, for example, a thermistor and a resistor connected in series between an analog power supply and an analog reference potential (analog ground). The temperature sensor 15 further has a comparator which compares the voltage of the node between the thermistor and the resistor with a predetermined voltage. The output terminal of the comparator serves as the output terminal of the temperature sensor 15. The predetermined voltage is set to a voltage corresponding to a predetermined temperature (for example, 80° C.) of the light-emitting element 121. When the temperature of the light-emitting element 121 detected by the thermistor is lower than the predetermined temperature, the temperature sensor 15 outputs, for example, a low (0 V) voltage from the comparator to the microprocessor 116. When the temperature of the light-emitting element 121 detected by the thermistor is higher than the predetermined temperature, the temperature sensor 15 outputs, for example, a high voltage (a high input voltage allowed by the microprocessor 116) from the comparator to the microprocessor 116.

The microprocessor 116 instructs the PWM signal generator 117 to change the duty ratio of the duty signal Sduty, in accordance with the level of the voltage input from the temperature sensor 15. When the microprocessor 116 receives a low voltage from the temperature sensor 15, it does not instruct the PWM signal generator 117 to change the duty ratio of the duty signal Sduty. When the microprocessor 116 receives a high voltage from the temperature sensor 15, it instructs the PWM signal generator 117 to raise the duty ratio of the duty signal Sduty. With this operation, since the amount of drive current flowing through the light-emitting element 121 increases, the emission intensity reduced with increased temperature of the light-emitting element 121 is compensated for. In this manner, the ultraviolet-emitting device 1 can compensate for the reduction in emission intensity due to factors associated with the temperature characteristics of the light-emitting element 121, independently of the reduction in emission intensity due to aging of the light-emitting element 121 (to be described in detail later).

The microprocessor 116 is configured to change the input bit values of the bias adjuster 111 and the offset adjuster 112 as needed in the setting state of a target drive current for the light-emitting element 121 and the state of a sterilization operation for the object to be sterilized by the light-emitting element 121. The microprocessor 116 is configured to further change the amplification factor of the amplifier 110 as needed in the setting state of a target drive current for the light-emitting element 121.

The light-emitting element driving circuit 11c has a controller 118 and a constant current source 119, as illustrated in FIG. 4. The controller 118 is configured to control the amount of current output from the constant current source 119, based on the duty signal Sduty input from the PWM signal generator 117. When the duty ratio of the duty signal Sduty input from the PWM signal generator 117 becomes lower, the controller 118 drives the constant current source 119 to decrease the amount of current to be output. When the duty ratio of the duty signal Sduty input from the PWM signal generator 117 becomes higher, the controller 118 drives the constant current source 119 to increase the amount of current to be output.

The light-emitting element 121 is connected in series with the constant current source 119. The positive electrode of the constant current source 119 is connected to the cathode of the light-emitting element 121 and the negative electrode of the constant current source 119 is connected to an analog reference potential (analog ground). The constant current source 119 is configured to output a predetermined amount of constant current from an analog power supply to the analog ground under the control of the controller 118. Since the light-emitting element 121 is connected in series with the constant current source 119, a constant current in an amount output from the constant current source 119 flows through the light-emitting element 121. The voltage value of the analog power supply applied to the anode of the light-emitting element 121 stays constant. Therefore, the intensity of ultraviolet rays emitted by the light-emitting element 121 is determined by the amount of constant current output from the constant current source 119. The ultraviolet-emitting device 1 sets the drive current flowing through the light-emitting element 121, that is, the current output from the constant current source 119 as an initial current in the setting state of a target drive current for the light-emitting element 121.

Figure 5:
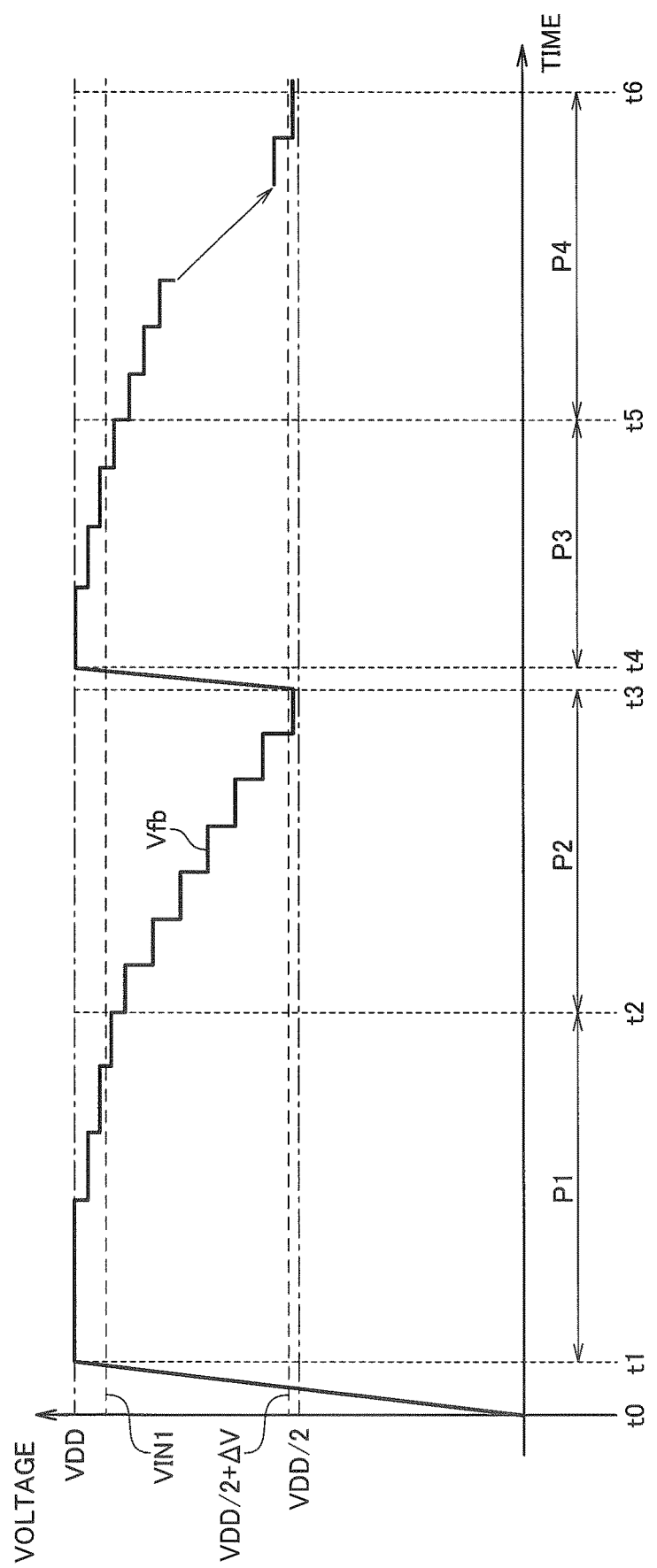
FIG. 5 is a chart illustrating an exemplary operation waveform in the target value setting state of the ultraviolet-emitting device 1 according to Embodiment 1 of the present invention.
Figure 6:
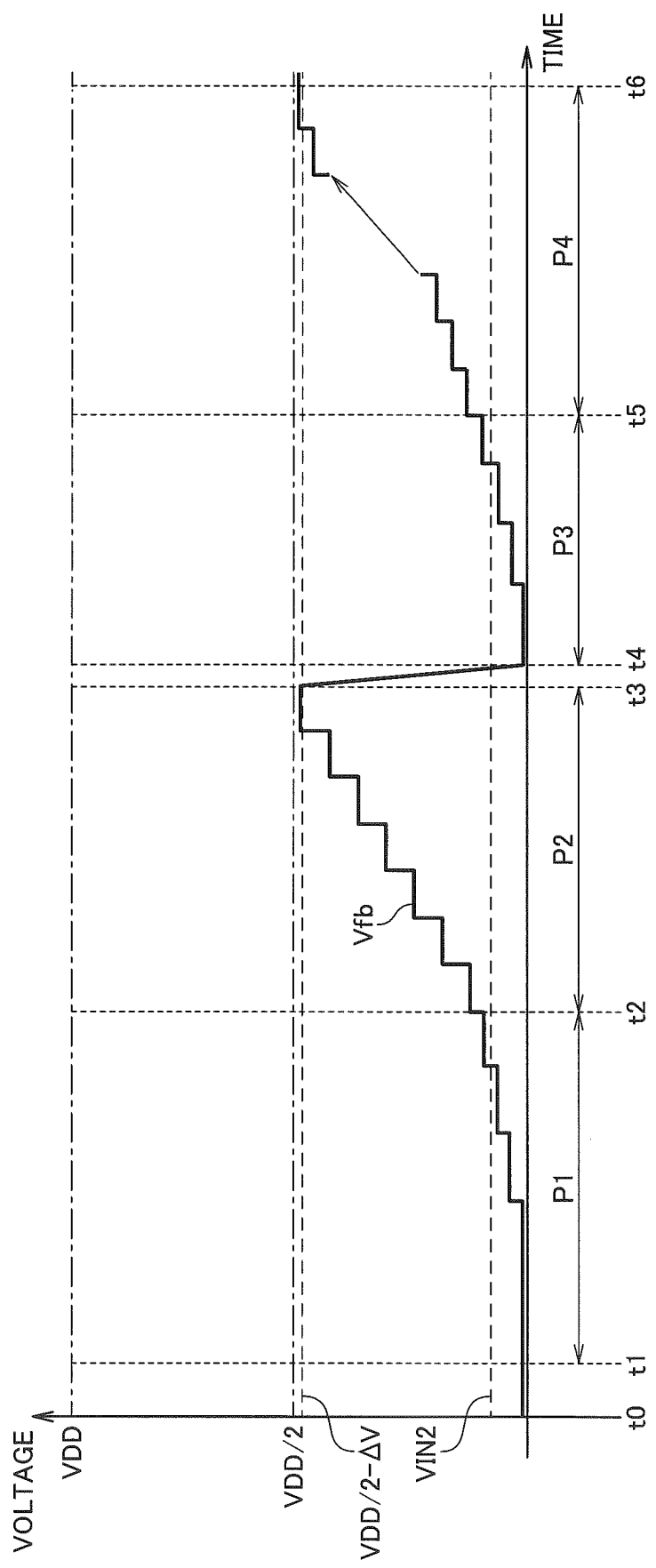
FIG. 6 is a chart illustrating an exemplary operation waveform in the target value setting state of the ultraviolet-emitting device 1 according to Embodiment 1 of the present invention.
Figure 7:
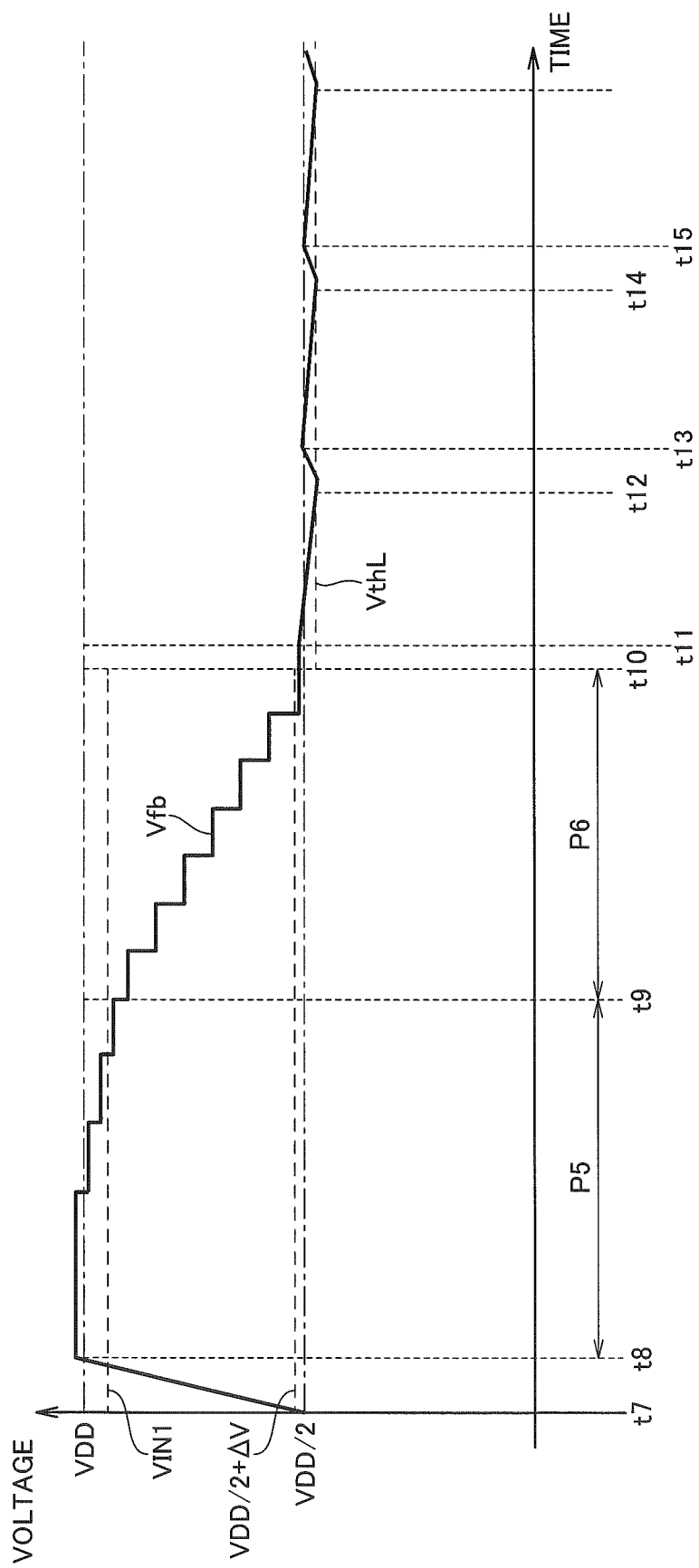
FIG. 7 is a chart illustrating an exemplary operation waveform when a shift is made from the target value setting state to the operation state of the ultraviolet-emitting device 1 according to Embodiment 1 of the present invention.

The operation of the ultraviolet-emitting device 1 will be described below with reference to FIGS. 5 to 7 in conjunction with FIGS. 1 and 4. FIGS. 5 and 7 or FIGS. 6 and 7 represent the operations of the ultraviolet-emitting device 1 in time sequence in the order of operations. The time scales represented in FIGS. 5 to 7 are different from the actual scales. In addition, referring to FIGS. 5 and 6, the number of fluctuations in feedback voltage Vfb is not equal to the actual number of bits, and parts of the feedback voltage Vfb are simply indicated by straight arrows.

The ultraviolet-emitting device 1 is configured to operate in two states: the target value setting state in which a target drive current for the light-emitting element 121 is set and the sterilization operation state in which the object to be sterilized is sterilized by the light-emitting element 121. In the target value setting state, the ultraviolet-emitting device 1 sets a target value for the light-emitting element 121 (in the present embodiment, a target value for the amount of drive current for the light-emitting element 121) by executing four steps.

First, in the target value setting state, the initial value of the amplification factor of the amplifier 110 is set to a maximum value. The input bit value is set so that the initial value of the voltage output from the bias adjuster 111 is ½ of the maximum voltage VDD. The input bit value is further set so that the initial value of the voltage output from the offset adjuster 112 is ½ of the maximum voltage VDD. The state identification signal Smode is set to "1."

After the end of the above-mentioned initial setting, as illustrated in FIG. 5, at time t0, the operations of the setting circuit 11a and the auto power control circuit 11b are started without operating the light-emitting element 121. Since the light-emitting element 121 is inactive, no fluorescence is generated by the fluorescent glass element 21, but a dark current, for example, flows through the photodetection element 14, and the current is therefore input from the photodetection element 14 to the I/V conversion circuit 114. Since the amplification factor of the amplifier 110 is set to a maximum value, the feedback voltage Vfb is output from the addition unit 113. At time t1, the feedback voltage Vfb takes a value larger than the maximum voltage VDD.

When a feedback voltage Vfb having a value larger than the maximum voltage VDD is output from the addition unit 113, the microprocessor 116 reduces the amplification factor of the amplifier 110 in steps of one grade in the first step.

The microprocessor 116 determines whether the feedback voltage Vfb has dropped to an input voltage VIN1 on the high side on which the operation of the microprocessor 116 is compensated for, every time the amplification factor of the amplifier 110 is reduced. The microprocessor 116 reduces the amplification factor of the amplifier 110 until it determines that the feedback voltage Vfb has dropped to the input voltage VIN1.

When the feedback voltage Vfb becomes lower than the input voltage VIN1 at, for example, time t2, in the second step the microprocessor 116 changes the input bit value in steps of one bit to lower the voltage output from the DAC for high-order bits provided in the offset adjuster 112. The microprocessor 116 determines whether the value of the feedback voltage Vfb falls within the range of ½ of the maximum voltage VDD to the error voltage (VDD/2+ΔV), every time the input bit value of the DAC for high-order bits is changed by one bit. When the microprocessor 116 determines that the value of the feedback voltage Vfb falls within the range of ½ of the maximum voltage VDD to the error voltage (VDD/2+ΔV) at, for example, time t3, it ends the change in input bit value of the DAC for high-order bits in the offset adjuster 112.

The ultraviolet-emitting device 1 executes the first and second steps again to adjust the offset voltage by the DAC for low-order bits provided in the offset adjuster 112. At time t3, the light-emitting element management circuit 11 sets the amplification factor of the amplifier 110 to a maximum value again. Thus, at time t4, the feedback voltage Vfb takes a value larger than the maximum voltage VDD.

When a feedback voltage Vfb having a value larger than the maximum voltage VDD is output from the addition unit 113, in the first step the light-emitting element management circuit 11 gradually reduces the amplification factor of the amplifier 110 to lower the feedback voltage Vfb to the input voltage VIN1 on the high side on which the operation of the microprocessor 116 is compensated for.

When the feedback voltage Vfb becomes lower than the input voltage VIN1 at, for example, time t5, in the second step the light-emitting element management circuit 11 changes the input bit value to lower the voltage output from the DAC for low-order bits provided in the offset adjuster 112. When the value of the feedback voltage Vfb falls within the range of ½ of the maximum voltage VDD to the error voltage (VDD/2+ΔV) at time t6, the light-emitting element management circuit 11 ends the change in input bit value of the DAC for low-order bits in the offset adjuster 112.

FIG. 5 illustrates an example in which the feedback voltage Vfb takes a value larger than the maximum voltage VDD when the operations of the setting circuit 11a and the auto power control circuit 11b are started in the target value setting state, but the feedback voltage Vfb may take a value smaller than the minimum voltage (0 V).

As illustrated in FIG. 6, at time t0, the operations of the setting circuit 11a and the auto power control circuit 11b are started without operating the light-emitting element 121. Since the light-emitting element 121 is inactive, no fluorescence is generated by the fluorescent glass element 21, but a dark current, for example, flows through the photodetection element 14, and the current is therefore input from the photodetection element 14 to the I/V conversion circuit 114. Since the amplification factor of the amplifier 110 is set to a maximum value, the feedback voltage Vfb is output from the addition unit 113. At time t1, the feedback voltage Vfb takes a value smaller than the minimum voltage (0 V).

When a feedback voltage Vfb having a value smaller than the minimum voltage (0 V) is output from the addition unit 113, in the first step the light-emitting element management circuit 11 gradually reduces the amplification factor of the amplifier 110 to raise the feedback voltage Vfb to an input voltage VIN2 on the low side on which the operation of the microprocessor 116 is compensated for.

When the feedback voltage Vfb becomes higher than the input voltage VIN2 at, for example, time t2, in the second step the microprocessor 116 changes the input bit value in steps of one bit to raise the voltage output from the DAC for high-order bits provided in the offset adjuster 112. When the microprocessor 116 determines that the value of the feedback voltage Vfb falls within the range of ½ of the maximum voltage VDD to the error voltage (VDD/2−ΔV) at time t3, it ends the change in input bit value of the DAC for high-order bits in the offset adjuster 112.

The ultraviolet-emitting device 1 executes the first and second steps again to adjust the offset voltage by the DAC for low-order bits provided in the offset adjuster 112. At time t3, the light-emitting element management circuit 11 sets the amplification factor of the amplifier 110 to a maximum value again. Thus, at time t4, the feedback voltage Vfb takes a value smaller than the minimum voltage (0 V).

When a feedback voltage Vfb having a value smaller than the minimum voltage (0 V) is output from the addition unit 113, in the first step the microprocessor 116 reduces the amplification factor of the amplifier 110 in steps of one grade to raise the feedback voltage Vfb to the input voltage VIN2 on the low side on which the operation of the microprocessor 116 is compensated for.

When the feedback voltage Vfb becomes higher than the input voltage VIN2 at, for example, time t5, in the second step the microprocessor 116 changes the input bit value in steps of one bit to raise the voltage output from the DAC for low-order bits provided in the offset adjuster 112. When the value of the feedback voltage Vfb falls within the range of ½ of the maximum voltage VDD to the error voltage (VDD/2−ΔV) at time t6, the change in input bit value of the DAC for low-order bits in the offset adjuster 112 is ended.

Periods P1 and P3 illustrated in FIGS. 5 and 6 correspond to the first step in which the amplification factor of the amplifier 110 is adjusted. Periods P2 and P4 illustrated in FIGS. 5 and 6 correspond to the second step in which an offset voltage included in the entire circuit constituting the ultraviolet-emitting device 1 is adjusted using the offset adjuster 112.

While the amplification factor of the amplifier 110 and the input bit values of the bias adjuster 111 and the offset adjuster 112 in the target value setting state are kept the same as in the state in which the second step has ended twice, a current having an initial value is supplied to the light-emitting element 121 at time t7. With this operation, the light-emitting element 121 starts its operation to emit ultraviolet rays. Since the fluorescent glass element 21 emits fluorescence upon being excited by ultraviolet rays incident from the light-emitting element 121, a current is input from the photodetection element 14 to the I/V conversion circuit 114. The current flowing from the photodetection element 14 to the I/V conversion circuit 114 in this case is larger than the amount of dark current by several orders of magnitude. Accordingly, at time t8, the feedback voltage Vfb output from the addition unit 113 takes a value larger than the maximum voltage VDD.

When a feedback voltage Vfb having a value larger than the maximum voltage VDD is output from the addition unit 113, in the third step the microprocessor 116 reduces the amplification factor of the amplifier 110 in steps of one grade to lower the feedback voltage Vfb to the input voltage VIN1 on the high side on which the operation of the microprocessor 116 is compensated for.

When the feedback voltage Vfb becomes lower than the input voltage VIN1 at, for example, time t9, in the fourth step the microprocessor 116 changes the input bit value in steps of one bit to lower the voltage output from the DAC provided in the bias adjuster 111. When the value of the feedback voltage Vfb falls within the range of ½ of the maximum voltage VDD to the error voltage (VDD/2+ΔV) at time t10, the change in input bit value of the DAC in the bias adjuster 111 is ended. The microprocessor 116 stores a digital signal, obtained by A/D-converting the feedback voltage Vfb at time t10 by the A/D converter 115, in a predetermined storage area as a target code. The microprocessor 116 sets an upper limit threshold code and a lower limit threshold code in a predetermined storage area, based on the stored target code. Thus, the ultraviolet-emitting device 1 completes the initial setting operation.

A period P5 illustrated in FIG. 7 corresponds to the third step in which the amplification factor of the amplifier 110 is adjusted when a current having an initial value has been supplied to the light-emitting element 121. A period P6 illustrated in FIG. 7 corresponds to the fourth step in which a DC bias included in the feedback voltage Vfb is adjusted when a current having an initial value has been supplied to the light-emitting element 121.

When the ultraviolet-emitting device 1 completes the initial setting operation, it sets the state identification signal Smode to "0." When the sterilization module M1 starts to sterilize the object to be sterilized at subsequent time t11, and the light-emitting element 121 continues to emit light, the light-emitting element 121 deteriorates over time and voltage vs. current characteristic of the light-emitting element 121 varies. Thus, at time t12, the feedback voltage Vfb becomes lower than a lower limit threshold voltage VthL corresponding to the lower limit threshold code.

The microprocessor 116 determines that the value of the digital signal input from the A/D converter 115 is smaller than the lower limit threshold code and the light-emitting element 121 maintains no desired emission intensity. Therefore, the microprocessor 116 outputs an instruction signal for increasing the drive current for the light-emitting element 121 to the PWM signal generator 117. Upon receiving the instruction signal, the PWM signal generator 117 generates a duty signal Sduty higher in duty ratio than the duty signal Sduty corresponding to the target code and outputs it to the light-emitting element driving circuit 11c. As a result, since the amount of current output from the constant current source 119 increases, the current flowing through the light-emitting element 121 also increases.

By repeating an operation for changing the duty ratio of the duty signal Sduty in the auto power control circuit 10, the amount of drive current flowing through the light-emitting element 121 increases, and the emission intensity returns to a desired intensity at, for example, time t13. Since the feedback voltage Vfb thus exceeds ½ of the maximum voltage VDD, the microprocessor 116 determines that the value of the digital signal input from the A/D converter 115 falls within the range of the upper limit threshold code and the lower limit threshold code, and the light-emitting element 121 maintains a desired emission intensity. Then, the microprocessor 116 stops outputting an instruction signal for increasing the drive current for the light-emitting element 121 to the PWM signal generator 117. The PWM signal generator 117 thus continuously outputs a duty signal Sduty having the last output duty ratio to the light-emitting element driving circuit 11c. As a result, the amount of current output from the constant current source 119 is maintained, and the amount of current flowing through the light-emitting element 121 is also maintained. The light-emitting element 121 maintains a desired emission intensity accordingly. In this manner, in the ultraviolet-emitting device 1, the microprocessor 116 can detect and compensate for the deterioration over time of the light-emitting element 121.

Assume that the feedback voltage Vfb becomes lower than the lower limit threshold voltage VthL at, for example, time t14, after time t13, upon continuation of the operation of the sterilization module M1. Then, the ultraviolet-emitting device 1 performs the same operation as that at time t12 to time t13. As a result, at time t15, the feedback voltage Vfb exceeds ½ of the maximum voltage VDD and the light-emitting element 121 emits light with a desired emission intensity again.

The ultraviolet-emitting device 1 performs initial setting of an operating point for the light-emitting element 121 to obtain not the maximum emission intensity of the light-emitting element 121 but a minimum emission intensity required to sterilize the object to be sterilized. Therefore, the ultraviolet-emitting device 1 can repeatedly compensate for the operation of the light-emitting element 121 until the operating point after compensation reaches an operating point having a maximum emission intensity even when the deterioration over time occurs in the light-emitting element 121.

The ultraviolet-emitting device 1 adjusts the offset voltage of the entire circuit constituting the ultraviolet-emitting device 1 in the target value setting state to set the feedback voltage Vfb to ½ of the maximum voltage VDD. Hence, even when the voltage fluctuates in the sterilization operation state, it is hardly probable that the feedback voltage Vfb will be higher than the maximum voltage VDD or lower than the minimum voltage (0 V). As a result, the ultraviolet-emitting device 1 can stabilize the sterilization operation in the sterilization module M1.

Assume that, after the operation of the light-emitting element 121 is started (after time t11 in FIG. 7), the lid portion 312 of the sterilization module M1 is opened, although not illustrated. Then, not only fluorescence emitted by the fluorescent glass element 21 but also external light strikes the photodetection element 14. The amount of external light is larger than the amount of fluorescence emitted by the fluorescent glass element 21 by several orders of magnitude. The feedback voltage Vfb is therefore higher than the maximum voltage VDD. Before the start of the operation of the light-emitting element 121, the microprocessor 116 receives a state identification signal Smode having value "0." The light-emitting element management circuit 11 stops the operation of the light-emitting element 121 by, for example, forcibly setting the value of the feedback voltage Vfb input to the A/D converter 115 to 0V or inputting a duty signal Sduty having zero duty ratio to the controller 118 of the light-emitting element driving circuit 11c. Hence, the ultraviolet-emitting device 1 can prevent ultraviolet rays from leaking out of the accommodation member 31.

As described above, the ultraviolet-emitting device 1 according to the present embodiment includes alight-emitting element 121 which emits ultraviolet rays, a fluorescent glass element 21 which is placed at a position, irradiated with the ultraviolet rays emitted by the light-emitting element 121, to protrude higher than the light-emitting element 121, and emits fluorescence in the visible range by excitation of the ultraviolet rays, a mounting board 314 on which the light-emitting element 121 is placed, and a photodetection element 14 which detects the intensity of the fluorescence emitted by the fluorescent glass element 21. Hence, the ultraviolet-emitting device 1 achieves prolonged life of the light-emitting element while maintaining a certain emission intensity of the light-emitting element.

The ultraviolet-emitting device 1 further includes a light-emitting element management circuit 11 which controls the light-emitting element 121, based on the intensity of the fluorescence detected by the photodetection element 14. The ultraviolet-emitting device 1 can automatically learn the initial value of the drive current for the light-emitting element 121 within the range of variation in the circuit system constituting the ultraviolet-emitting device 1 and operate to maintain the emission intensity (output power) of the light-emitting element 121 constant when the deterioration over time of the light-emitting element 121 falls within the expected range.

The ultraviolet-emitting device 1 can stop the light-emitting element 121 when a high power exceeding the gain of the circuit system constituting the ultraviolet-emitting device 1 is input (that is, when the lid portion 312 of the sterilization module M1 is opened during a sterilization operation). Hence, the ultraviolet-emitting device 1 can serve as a safety device.

The ultraviolet-emitting device 1 uses the fluorescent glass element 21 to keep ultraviolet rays from being directly input to the photodetection element 14. This can prevent the resin used to mold the detection unit of the photodetection element 14 from deteriorating upon irradiation with ultraviolet rays. Since the feedback voltage Vfb can hardly include variations based on the deterioration of the photodetection element 14, the deterioration of the light-emitting element 121 can be accurately compensated for based on the feedback voltage Vfb.

The ultraviolet-emitting device 1 can use the fluorescent glass element 21 to convert 265-nm-wavelength ultraviolet rays emitted by the light-emitting element 121 into 580-nm-wavelength fluorescence and detect the ultraviolet rays emitted by the light-emitting element 121. This allows the use of a highly sensitive photodetection element 14 and, in turn, allows stabilization of the operation of the light-emitting element management circuit 11.

Embodiment 2

Embodiment 2 (including Embodiments 2-1 to 2-3) of the present invention relates to an ultraviolet-emitting device including a light-emitting element which emits light having wavelengths shorter than the visible range.

It is an object of the present embodiment to provide an ultraviolet-emitting device capable of preventing a management circuit which controls a light-emitting element from deteriorating by ultraviolet rays emitted by the light-emitting element, in addition to the above-described object.

Embodiment 2-1

An ultraviolet-emitting device according to Embodiment 2-1 of the present invention will be described below with reference to FIGS. 8 and 9. The schematic configuration of an ultraviolet-emitting device 2 according to the present embodiment will be described first with reference to FIGS. 8 and 9. In the ultraviolet-emitting device 2 according to the present embodiment, and an ultraviolet-emitting device 3 according to Embodiment 2-2 and an ultraviolet-emitting device 4 according to Embodiment 2-3 (both will be described later), the same reference numerals denote components exhibiting the same actions and functions as those of the components in above-described Embodiment 1.

Figure 8:
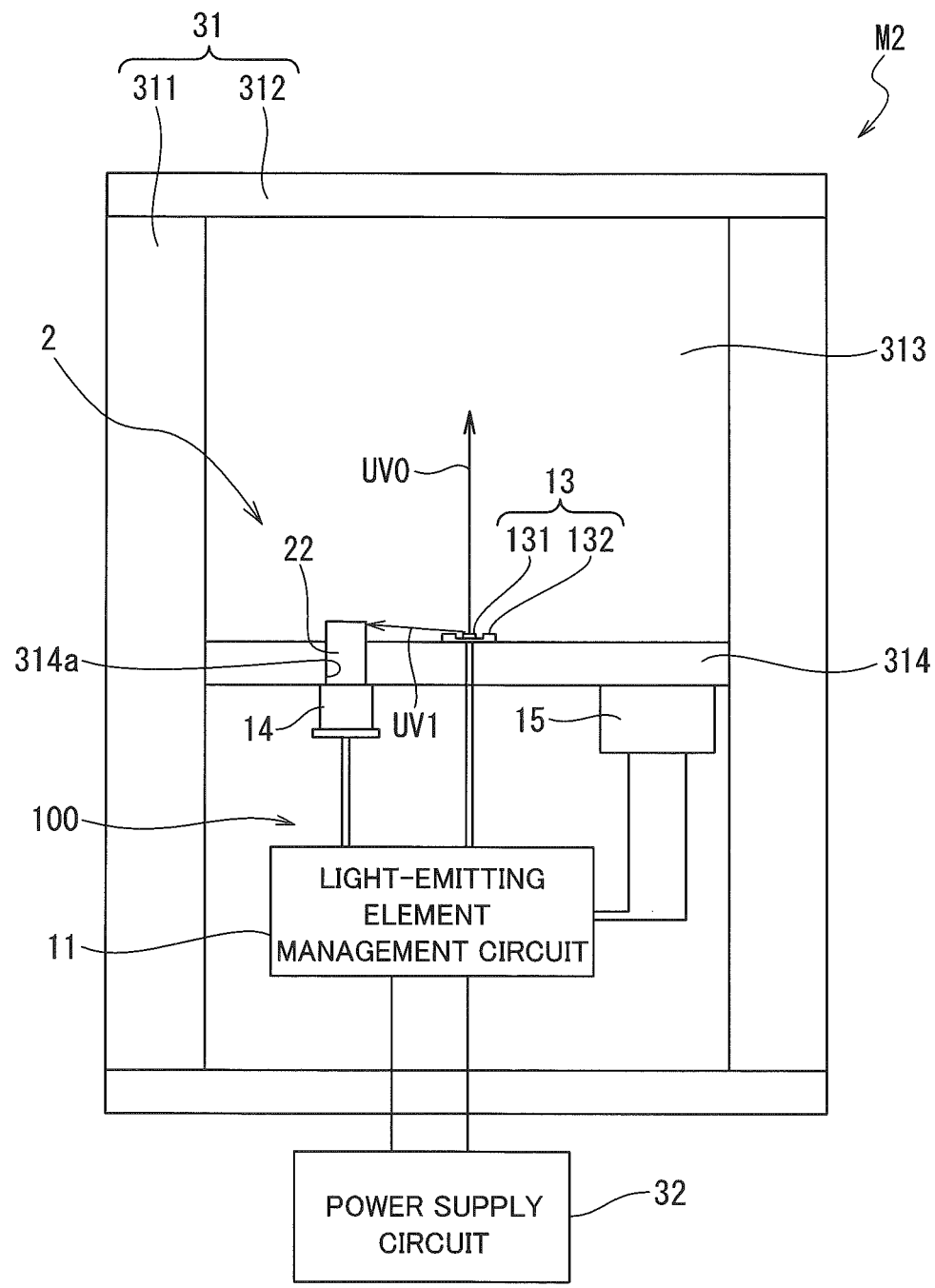
FIG. 8 is a diagram typically illustrating the schematic configuration of a sterilization module M2 including an ultraviolet-emitting device 2 according to Embodiment 2-1 of the present invention.

As illustrated in FIG. 8, the ultraviolet-emitting device 2 according to the present embodiment includes a light-emitting element 131 which emits ultraviolet rays, a mounting board (an example of a board) 314 on which the light-emitting element 131 is placed, and a fluorescent glass element 22 placed at a position irradiated with ultraviolet rays UV1 emitted by the light-emitting element 131, and placed in a through hole 314a formed through the mounting board 314, and emitting fluorescence in the visible range by excitation of an ultraviolet rays. The light-emitting element 131 is provided in a ceramic package 132 including a ceramic board. The light-emitting element 131 is mounted on the ceramic board. The light-emitting element 131 and the ceramic package 132 are provided in a light source 13. At least a part of the mounting board 314 is made of a member absorbing or reflecting ultraviolet rays. The ultraviolet-emitting device 2 includes an electronic component group 100 on the opposite side of a placement side of the light-emitting element 131 with respect to the mounting board 314.

The electronic component group 100 may include at least one of a photodetection element 14 which detects at least one of the presence or the absence of the emission and emission intensity (fluorescence intensity) of light emitted by the fluorescent glass element 22, a light-emitting element management circuit 11 which adjusts at least one of the presence or the absence of the emission and emission intensity of ultraviolet rays emitted by the light-emitting element 131, and a temperature sensor 15 (to be described in detail later). In the ultraviolet-emitting device 2 according to the present embodiment, the electronic component group 100 includes the photodetection element 14, the light-emitting element management circuit 11, and the temperature sensor 15. The light-emitting element management circuit 11 corresponds to an example of an element which can perform at least one of sending of at least one of the presence or the absence of the emission and emission intensity of ultraviolet rays emitted by the light-emitting element 131 to the outside, control (for example, ON/OFF control) to cause the light-emitting element 131 to emit ultraviolet rays with a desired emission intensity, and adjustment of the ultraviolet rays emitted by the light-emitting element 131 to a desired emission intensity. The light-emitting element management circuit 11 is configured to control the light-emitting element 131, based on the fluorescence intensity detected by the photodetection element 14.

The photodetection element 14, the light-emitting element management circuit 11, and the temperature sensor 15 correspond to examples of electronic components. In this manner, the electronic component group 100 has a plurality of electronic components. In other words, a plurality of electronic components are provided in the ultraviolet-emitting device 2 to form the electronic component group 100. As illustrated in FIG. 8, the electronic component group 100 may be disposed in whole on the opposite side of a placement side of the light-emitting element 131 with respect to the mounting board 314 without being partly exposed on or protruded to the placement side of the light-emitting element 131. Furthermore, each of the photodetection element 14, the light-emitting element management circuit 11, the temperature sensor 15, and other electronic components constituting the electronic component group 100 may be disposed in whole on the opposite side of the placement side of the light-emitting element 131 with respect to the mounting board 314 without being partly exposed on or being partly protruded to the placement side of the light-emitting element 131.

The ultraviolet-emitting device 2 is accommodated in a box-shaped or cylindrical sterilization module M2. The sterilization module M2 includes an accommodation member 31 which can accommodate an object (not illustrated) to be sterilized by the ultraviolet-emitting device 2 and the light-emitting element 131 in an external light-shielded state. The sterilization module M2 includes an accommodation space 313 which can accommodate the ultraviolet-emitting device 2 and the object to be sterilized. The sterilization module M2 is configured to sterilize running water (an example of an object to be sterilized) flowing from one outside into the accommodation space 313, using ultraviolet rays emitted by the light-emitting element 131, and guide the sterilized running water to the other outside.

The accommodation member 31 has a main body portion 311 having the accommodation space 313, and a lid portion 312 which can block incidence of external light on the accommodation space 313. The main body portion 311 has a box shape open at its one end. The lid portion 312 is provided on the main body portion 311 to allow opening and closing of one end of the main body portion 311. The sterilization module M2 has its lid portion 312 opened to open one end of the main body portion 311, and, after the ultraviolet-emitting device 2 is accommodated in the accommodation space 313, has its lid portion 312 closed to form a closed space in the accommodation space 313. After a closed space is formed in the accommodation space 313, running water flows into the sterilization module M2.

The accommodation space 313 is surrounded by the main body portion 311 and the lid portion 312. The object to be sterilized accommodated in the accommodation space 313 is sterilized with ultraviolet rays emitted by the light-emitting element 131. In this manner, the light-emitting element 131 is provided to allow irradiation of the object to be sterilized with ultraviolet rays. Hence, the ultraviolet-emitting device 2 can serve as a sterilizer and can be used as such.

The sterilization module M2 has in the accommodation space 313, a mounting board 314 on which the light source 13 and the like is placed. The mounting board 314 corresponds to a board on which the light-emitting element 131 is placed. The mounting board 314 supports not only the light source 13 but also the fluorescent glass element 22, the photodetection element 14, and the temperature sensor 15 mounted on it. The mounting board 314 is made of a material (for example, aluminum) absorbing or reflecting ultraviolet rays and having a low thermal resistance. Hence, the mounting board 314 serves both as a preventive member which prevents ultraviolet rays from striking the opposite side of the placement side of the light-emitting element 131 with respect to the mounting board 314, and as a heat radiation member for dissipating heat generated by the light-emitting element 131.

The positional relationship between the light-emitting element 131 and the electronic component group 100 will be described herein with reference to FIG. 9. FIG. 9 represents the regions of a setting circuit 11a, an APC circuit 11b, and a light-emitting element driving circuit 11c (all will be described in detail later) constituting the light-emitting element management circuit 11, the photodetection element 14, and the temperature sensor 15. The positions of the setting circuit 11a, the APC circuit 11b, the light-emitting element driving circuit 11c, the photodetection element 14, and the temperature sensor 15 relative to each other are not limited to those represented in FIG. 9 and may be changed as appropriate.

Figure 9:
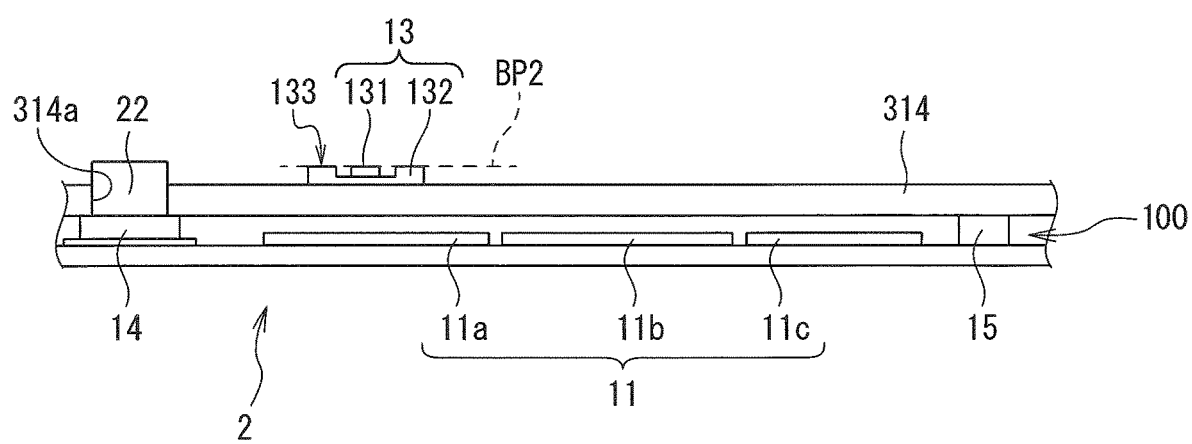
FIG. 9 is a view schematically illustrating the positional relationship between a light-emitting element 131 and a light-emitting element management circuit 11 provided in the ultraviolet-emitting device 2 according to Embodiment 2-1 of the present invention.

The light-emitting element management circuit 11 is placed on the opposite side of a surface (to be sometimes referred to as an "element mounting surface" hereinafter) on the side (placement side) where the light-emitting element 131 is placed with respect to the mounting board 314, as illustrated in FIG. 9. The photodetection element 14 and the temperature sensor 15 are also placed on the opposite side of the element mounting surface of the mounting board 314. The light-emitting element 131 has a predetermined directivity. Ultraviolet rays emitted by the light-emitting element 131 may be partially guided to the mounting board 314. However, the mounting board 314 includes at least a part (for example, a portion corresponding to the region of the electronic component group 100) made of a member absorbing or reflecting ultraviolet rays. Ultraviolet rays emitted by the light-emitting element 131 are blocked by the mounting board 314 and do not strike the opposite side of the element mounting surface. This prevents ultraviolet rays from striking the light-emitting element management circuit 11 that are electronic components included in the electronic component group 100, the photodetection element 14, and the temperature sensor 15. As a result, even when a part of each of the light-emitting element management circuit 11, the photodetection element 14, and the temperature sensor 15 is made of a material deteriorated by ultraviolet rays, such as a resin, they are prevented from being deteriorated by ultraviolet rays emitted by the light-emitting element 131.

The fluorescent glass element 22 is inserted into the through hole 314a and is arranged through the mounting board 314, as illustrated in FIG. 9. The fluorescent glass element 22 is disposed so as to protrude from the mounting board 314 to a level higher than the light-emitting element 131. Therefore, the fluorescent glass element 22 is partially exposed on the element mounting surface of the mounting board 314. The fluorescent glass element 22 is adjacent to the light-emitting element 131. With this arrangement, the ultraviolet rays UV1 emitted by the light-emitting element 131 can be guided to the fluorescent glass element 22. The fluorescent glass element 22 is also partially exposed on a surface (to be sometimes referred to as a "mounting back surface" hereinafter) opposite to the element mounting surface of the mounting board 314. The fluorescent glass element 22 can thus guide fluorescence in the visible range emitted by excitation of the ultraviolet rays UV1 to the photodetection element 14 placed below the mounting back surface of the mounting board 314. The fluorescent glass element 22 protrudes to the side where the light-emitting element 131 is placed from the mounting board 314 and a part of the fluorescent glass element 22 is arranged the side where the light-emitting element 131 is placed. Accordingly, the fluorescent glass element 22 corresponds to neither an electronic component that is placed on the opposite side of the placement side of the light-emitting element 131 with respect to the mounting board 314 nor an electronic component constituting the electronic component group 100.

Referring back to FIG. 8, the sterilization module M2 includes a power supply circuit 32 which supplies power to the ultraviolet-emitting device 2 and the like. The power supply circuit 32 is connected to a power supply cable connected to the ultraviolet-emitting device 2 and routed out of the accommodation member 31.

The fluorescent glass element 22 will be described below.

As illustrated in FIG. 9, the fluorescent glass element 22 protrudes from the mounting board 314 to a level higher than the light-emitting element 131 with respect to an upper surface 133 of the ceramic package 132 accommodating the light-emitting element 131 and is adjacent to the light-emitting element 131 or adjacent to the light source 13. The "upper surface" may be defined herein, for example, as the surface of the ceramic package 132 opposite to a surface (element mounting surface) which allows the ceramic package 132 to come into contact with the mounting board 314, or as a virtual plane BP2 including this surface of the ceramic package 132.

The light-emitting element 131 emits ultraviolet rays having a distribution of luminous intensity (see FIG. 2) similar to, for example, the Lambert distribution of luminous intensity. The light distribution pattern possesses a directivity having a half-power angle of about 50°. By placing the fluorescent glass element 22 adjacent to the light-emitting element 131 to protrude higher than the light-emitting element 131, the fluorescent glass element 22 is partially included in the region irradiated with ultraviolet rays by the light-emitting element 131. The fluorescent glass element 22 is placed so as not to cross ultraviolet rays UV0 (see FIG. 8) having a highest intensity on the optical axis of ultraviolet rays emitted by the light-emitting element 131. The fluorescent glass element 22 crosses ultraviolet rays UV1 having a relative radiation intensity lower than the relative radiation intensity in terms of the half-power angle of ultraviolet rays emitted by the light-emitting element 131. With this arrangement, the ultraviolet-emitting device 2 can guide ultraviolet rays emitted by the light-emitting element 131 to the fluorescent glass element 22 while suppressing attenuation of the ultraviolet rays impinging on the object to be sterilized. Hence, the sterilization module M2 can prevent degradation in sterilization efficiency of the object to be sterilized.

The fluorescent glass element 22 exhibits a fluorescence spectrum having a maximum peak in a wavelength range in which the photodetection element 14 has a relatively high detection sensitivity. The fluorescent glass element 22 exhibits a fluorescence spectrum having a maximum peak at a wavelength of, for example, 540 nm and is configured to emit green fluorescence. The photodetection element 14 exhibits a maximum sensitivity at a wavelength of, for example, 560 nm and detection characteristics having a full width at half maximum of about 120 nm. Hence, the photodetection element 14 can receive light emitted by the fluorescent glass element 22 even when ultraviolet rays are applied to the fluorescent glass element 22 in a small amount and the fluorescent glass element 22 emits low-intensity fluorescence.

The fluorescent glass element 22 has, for example, a quadrangular prismatic shape. The shape of the fluorescent glass element 22 is not limited to this and may be prismatic shapes other than a quadrangular prismatic shape, circular and elliptical shapes and the like. The fluorescent glass element 22 may have its one end face inclined and exposed on the element mounting surface of the mounting board 314 to allow nearly perpendicular incidence of the ultraviolet rays UV1. The fluorescent glass element 22 may include, at its one end, an inclined surface lower in the direction away from the light-emitting element 131.

The circuit configuration of the ultraviolet-emitting device 2 will be described. The ultraviolet-emitting device 2 has the same as the circuit configuration of the ultraviolet-emitting device 1 according to above-described Embodiment 1, except that the fluorescent glass element 22 is provided instead of the fluorescent glass element 21 and the light source 13 is provided instead of the light source 12. Therefore, the circuit configuration of the ultraviolet-emitting device 2 will be described with reference to FIG. 4. In addition, when referring to FIG. 4, the fluorescent glass element 21 is read as the fluorescent glass element 22, and the light emitting element 121 is read as the light emitting element 131.

The ultraviolet-emitting device 2 includes a light-emitting element 131, a fluorescent glass element 22, and an electronic component group 100, as illustrated in FIG. 4. A photodetection element 14, a temperature sensor 15, and a light-emitting element management circuit 11 are included in the electronic component group 100.

The light-emitting element 131 is designed as, for example, an LED (Light Emitting Diode) which emits ultraviolet rays. The light-emitting element 131 has its anode connected to, for example, an analog power supply and its cathode connected to, for example, the positive electrode of a constant current source 119 (to be described in detail later) provided in a light-emitting element driving circuit 11c.

The fluorescent glass element 22 emits, for example, green fluorescence (having a wavelength of, for example, 560 nm) upon being excited by ultraviolet rays (having a wavelength of, for example, 265 nm) emitted by the light-emitting element 131, as described above. In other words, the fluorescent glass element 22 converts 265-nm-wavelength light into 560-nm-wavelength light.

The photodetection element 14 is designed as, for example, a PD (Photodiode). The photodetection element 14 has its cathode connected to, for example, an analog power supply and its anode connected to, for example, a current-to-voltage conversion circuit 114 (to be described in detail later) provided in an auto power control circuit 11b. The photodetection element 14 is configured to convert the fluorescence emitted by the fluorescent glass element 22 into a current and output it to the current-to-voltage conversion circuit 114.

The light-emitting element management circuit 11 has a setting circuit (an example of a setting unit) 11a which sets a target value for causing the light-emitting element 131 to emit light with a desired emission intensity, and an APC (Auto Power Control) circuit (an example of an automatic power controller) 11b which maintains the light-emitting element 131 at the desired emission intensity, as illustrated in FIG. 4. The target value set by the setting circuit 11a is the value of the drive current for the light-emitting element 131, although details will be described later. The light-emitting element management circuit 11 further has a light-emitting element driving circuit (an example of a driver) which drives the light-emitting element 131.

The setting circuit 11a has an amplifier 110 which amplifies a voltage based on a detection signal detected by the photodetection element 14, a bias adjuster 111 which adjusts the DC bias of the voltage output from the amplifier 110, and an offset adjuster 112 which adjusts an offset voltage included in the voltage output from the amplifier 110. The setting circuit 11a further has an addition unit 113 which sums the voltage output from the amplifier 110, that output from the bias adjuster 111, and that output from the offset adjuster 112.

The amplifier 110 has its input terminal connected to the output terminal of the current-to-voltage conversion circuit 114 provided in the auto power control circuit 11b. The amplifier 110 has its output terminal connected to one of the three input terminals of the addition unit 113. The addition unit 113 has its one remaining terminal connected to the output terminal of the bias adjuster 111 and its other remaining terminal connected to the output terminal of the offset adjuster 112. The addition unit 113 has its output terminal connected to the input terminal of an analog-to-digital converter 115 (to be described in detail later) provided in the auto power control circuit 11b. The bias adjuster 111 has its input terminal, to receive an input bit signal, connected to a predetermined output terminal of a microprocessor 116 (to be described in detail later) provided in the auto power control circuit 11b. The offset adjuster 112 has its input terminal, to receive an input bit signal, connected to a predetermined output terminal of the microprocessor 116.

The amplifier 110 is designed as, for example, a PGA (Programmable Gain Amplifier). The amplifier 110 is configured to amplify a voltage input from the current-to-voltage conversion circuit 114 and output it to the addition unit 113. The amplification factor (gain) of the amplifier 110 is adjusted as needed upon setting of a target drive current for causing the light-emitting element 131 to emit light with a desired emission intensity (to be sometimes simply referred to as "a target drive current for the light-emitting element 131" hereinafter) and at the start of the operation of the light-emitting element 131, although details will be described later.

The bias adjuster 111 is designed as, for example, a digital-to-analog conversion circuit (Digital-to-Analog Converter: DAC). In the present embodiment, the bias adjuster 111 includes a DAC for high-order 8 bits and a DAC for low-order 8 bits. The bias adjuster 111 allows bias adjustment of the voltage output from the amplifier 110, using 16 bits accordingly. Hence, the bias adjuster 111 allows bias adjustment with a sufficient resolution even when a small amount of light is detected by the photodetection element 14. The number of input bits of the bias adjuster 111 is not limited to 16 bits and may be set as appropriate in accordance with the amount of light detected by the photodetection element 14. The voltage output from the bias adjuster 111 (that is, the input bit value) is adjusted as needed at the start of the operation of the light-emitting element 131, although details will be described later.

The offset adjuster 112 is designed as, for example, a digital-to-analog conversion circuit (Digital-to-Analog Converter: DAC). In the present embodiment, the offset adjuster 112 includes a DAC for high-order 8 bits and a DAC for low-order 8 bits. The offset adjuster 112 allows offset adjustment of the voltage output from the amplifier 110, using 16 bits accordingly. Hence, the offset adjuster 112 allows offset adjustment with a sufficient resolution even when a small amount of light is detected by the photodetection element 14. The number of input bits of the offset adjuster 112 is not limited to 16 bits and may be set as appropriate in accordance with the amount of light detected by the photodetection element 14. The offset adjuster 112 is used to adjust an offset voltage generated by the entire circuit constituting the ultraviolet-emitting device 1. The voltage output from the offset adjuster 112 (that is, the input bit value) is adjusted as needed upon setting of a target drive current for the light-emitting element 131, although details will be described later.

The addition unit 113 is configured to output to the auto power control circuit 1ib, a sum voltage obtained by summing the voltage output from the amplifier 110, the voltage output from the bias adjuster 111, and the voltage output from the offset adjuster 112. In other words, the addition unit 113 has a 3-input/1-output configuration. The addition unit 113 can have various circuit configurations. For example, the addition unit 113 may have two 2-input/1-output operational amplifiers, one of which is configured to sum the voltage output from the bias adjuster 111 and the voltage output from the offset adjuster 112 and the other of which is configured to sum the voltage output from the former operational amplifier and the voltage output from the amplifier 110. Upon setting of a target drive current for the light-emitting element 131, the addition unit 113 finally outputs a voltage based on the emission intensity of the light-emitting element 131 driven by the target drive current as a feedback voltage Vfb. The addition unit 113 further outputs a voltage based on the emission intensity of the light-emitting element 131 as a feedback voltage Vfb during a sterilization operation for the object to be sterilized by the light-emitting element 131.

The auto power control circuit 11b has a current-to-voltage (to be sometimes referred to as "I/V" hereinafter) conversion circuit 114 having its input terminal connected to the anode of the photodetection element 14, as illustrated in FIG. 4. The I/V conversion circuit 114 is implemented using, for example, a current input operational amplifier, although a detailed circuit configuration will not be described. The output terminal of the I/V conversion circuit 114 is connected to the noninverting input terminal of the amplifier 110 provided in the setting circuit 11a. The I/V conversion circuit 114 is configured to convert a current input from the photodetection element 14 into a voltage and output it to the amplifier 110.

The auto power control circuit 11b has an analog-to-digital converter ("analog-to-digital" will sometimes be abbreviated as "A/D" hereinafter) 115 which converts an analog signal output from the setting circuit 11a into a digital signal. The auto power control circuit 11b also has a microprocessor (an example of a determination unit) 116 which determines whether the light-emitting element 131 maintains a desired emission intensity, based on the digital signal converted by the A/D converter 115. The auto power control circuit 11b further includes a pulse-width modulated signal generator (an example of a generator) 117 which generates a PWM (Pulse Width Modulation) signal (an example of a control signal) for controlling the light-emitting element driving circuit (an example of a driver) 11c, based on an instruction from the microprocessor 116. Referring to FIG. 4, the microprocessor is symbolized by "µP." Pulse width modulation will sometimes be abbreviated as "PWM" hereinafter. The auto power control circuit 11b determines whether the light-emitting element 131 operates with a desired emission intensity, based on the feedback voltage Vfb during a sterilization operation, although details will be described later.

The output terminal of the A/D converter 115 is connected to a predetermined input terminal, to receive a bit signal, of the microprocessor 116. The predetermined output terminal of the microprocessor 116 is connected to the input terminal of the PWM signal generator 117. The output terminal of the PWM signal generator 117 is connected to the input terminal of a controller 118 (to be described in detail later) provided in the light-emitting element driving circuit 11c.

The A/D converter (Analog-to-Digital Converter: ADC) 115 converts the feedback voltage Vfb of an analog signal input from the addition unit 113 provided in the setting circuit 11a into a digital signal and outputs it to the microprocessor 116.

The microprocessor 116 stores a digital signal, input from the A/D converter 115 when setting of a target drive current for the light-emitting element 131 is complete, in a predetermined storage area as a target code. The target code is the condition of a drive current for driving the light-emitting element 131 with a desired emission intensity. After storing a target code, the microprocessor 116 stores the allowable operating range of the light-emitting element 131 in a predetermined storage area as a threshold code. The microprocessor 116 sets an upper limit threshold code defining the upper limit and a lower limit threshold code defining the lower limit of the allowable operating range of the light-emitting element 131.

The microprocessor 116 compares the digital signal input from the A/D converter 115 with the target code and the threshold code during a sterilization operation for the object to be sterilized by the light-emitting element 131. When the value of the input digital signal falls within the range between the target code and the threshold code, the microprocessor 116 determines that the light-emitting element 131 maintains a desired emission intensity. When the value of the input digital signal falls outside the range between the target code and the threshold code, the microprocessor 116 determines that the light-emitting element 131 maintains no desired emission intensity. The microprocessor 116 outputs no special instruction signal to the PWM signal generator 117 when it determines that the light-emitting element 131 maintains a desired emission intensity. The microprocessor 116 outputs a signal for instructing the PWM signal generator 117 to change the drive current when it determines that the light-emitting element 131 maintains no desired emission intensity. When the value of the input digital signal is larger than the upper limit threshold code, the microprocessor 116 outputs a signal for an instruction to decrease the amount of drive current to the PWM signal generator 117.

When the value of the input digital signal is smaller than the lower limit threshold code, the microprocessor 116 outputs a signal for an instruction to increase the amount of drive current to the PWM signal generator 117. In this manner, the ultraviolet-emitting device 1 performs control to allow the light-emitting element 131 to maintain a desired emission intensity by feeding back the emission intensity of the light-emitting element 131 during a sterilization operation for the object to be sterilized by the light-emitting element 131.

The microprocessor 116 receives a state identification signal Smode, as illustrated in FIG. 4. The state identification signal Smode is used to identify whether the operation state of the ultraviolet-emitting device 1 is the state of a sterilization operation for the object to be sterilized by the light-emitting element 131 or the setting state of a target drive current for the light-emitting element 131. When the state identification signal Smode is "0," the microprocessor 116 determines that, for example, the state of a sterilization operation for the object to be sterilized by the light-emitting element 131 has been set. When the state identification signal Smode is "1," the microprocessor 116 determines that, for example, the setting state of a target drive current for the light-emitting element 131 has been set.

In other words, the microprocessor 116 can determine whether the light-emitting element 131 is active, based on the signal level of the state identification signal Smode. Therefore, when the light-emitting element management circuit 11 determines that external light has entered the accommodation member 31 that can accommodate the object to be sterilized and the light-emitting element 131, during the operation of the light-emitting element 131 while the object to be sterilized is ready to be sterilized, it stops the operation of the light-emitting element 131. When the sterilization module M1 is used in an unusual manner in the state of a sterilization operation for the object to be sterilized by the light-emitting element 131, the light-emitting element management circuit 11 immediately stops the light-emitting element 131, based on the state identification signal Smode. Hence, the ultraviolet-emitting device 1 can prevent ultraviolet rays from leaking out while the sterilization module M1 sterilizes the object to be sterilized.

The PWM signal generator 117 outputs a duty signal Sduty to the light-emitting element driving circuit 11c, based on the instruction signal input from the microprocessor 116. When a signal for an instruction to decrease the drive current is input from the microprocessor 116, the PWM signal generator 117 outputs a duty signal Sduty lower in duty ratio than the last output duty signal Sduty to the light-emitting element driving circuit 11c. When a signal for an instruction to increase the drive current is input from the microprocessor 116, the PWM signal generator 117 outputs a duty signal Sduty higher in duty ratio than the last output duty signal Sduty to the light-emitting element driving circuit 11c.

The ultraviolet-emitting device 1 includes a temperature sensor (an example of a temperature detector) 15 which detects the temperature of the light-emitting element 131. The auto power control circuit 11b controls the light-emitting element driving circuit 11c, based on the temperature detected by the temperature sensor 15. The output terminal of the temperature sensor 15 is connected to a predetermined input terminal of the microprocessor 116.

The temperature sensor 15 has, for example, a thermistor and a resistor connected in series between an analog power supply and an analog reference potential (analog ground). The temperature sensor 15 further has a comparator which compares the voltage of the node between the thermistor and the resistor with a predetermined voltage. The output terminal of the comparator serves as the output terminal of the temperature sensor 15. The predetermined voltage is set to a voltage corresponding to a predetermined temperature (for example, 80° C.) of the light-emitting element 131. When the temperature of the light-emitting element 131 detected by the thermistor is lower than the predetermined temperature, the temperature sensor 15 outputs, for example, a low (0 V) voltage from the comparator to the microprocessor 116. When the temperature of the light-emitting element 131 detected by the thermistor is higher than the predetermined temperature, the temperature sensor 15 outputs, for example, a high voltage (a high input voltage allowed by the microprocessor 116) from the comparator to the microprocessor 116.

The microprocessor 116 instructs the PWM signal generator 117 to change the duty ratio of the duty signal Sduty, in accordance with the level of the voltage input from the temperature sensor 15. When the microprocessor 116 receives a low voltage from the temperature sensor 15, it does not instruct the PWM signal generator 117 to change the duty ratio of the duty signal Sduty. When the microprocessor 116 receives a high voltage from the temperature sensor 15, it instructs the PWM signal generator 117 to raise the duty ratio of the duty signal Sduty. With this operation, since the amount of drive current flowing through the light-emitting element 131 increases, the emission intensity reduced with increased temperature of the light-emitting element 131 is compensated for. In this manner, the ultraviolet-emitting device 1 can compensate for the reduction in emission intensity due to factors associated with the temperature characteristics of the light-emitting element 131, independently of the reduction in emission intensity due to aging of the light-emitting element 131 (to be described in detail later).

The microprocessor 116 is configured to change the input bit values of the bias adjuster 111 and the offset adjuster 112 as needed in the setting state of a target drive current for the light-emitting element 131 and the state of a sterilization operation for the object to be sterilized by the light-emitting element 131. The microprocessor 116 is configured to further change the amplification factor of the amplifier 110 as needed in the setting state of a target drive current for the light-emitting element 131.

The light-emitting element driving circuit 11c includes a controller 118 and a constant current source 119, as illustrated in FIG. 4. The controller 118 is configured to control the amount of current output from the constant current source 119, based on the duty signal Sduty input from the PWM signal generator 117. When the duty ratio of the duty signal Sduty input from the PWM signal generator 117 becomes lower, the controller 118 drives the constant current source 119 to decrease the amount of current to be output. When the duty ratio of the duty signal Sduty input from the PWM signal generator 117 becomes higher, the controller 118 drives the constant current source 119 to increase the amount of current to be output.

The light-emitting element 131 is connected in series with the constant current source 119. The positive electrode of the constant current source 119 is connected to the cathode of the light-emitting element 131 and the negative electrode of the constant current source 119 is connected to an analog reference potential (analog ground). The constant current source 119 is configured to output a predetermined amount of constant current from an analog power supply to the analog ground under the control of the controller 118. Since the light-emitting element 131 is connected in series with the constant current source 119, a constant current in an amount output from the constant current source 119 flows through the light-emitting element 131. The voltage value of the analog power supply applied to the anode of the light-emitting element 131 stays constant. Therefore, the intensity of ultraviolet rays emitted by the light-emitting element 131 is determined by the amount of constant current output from the constant current source 119. The ultraviolet-emitting device 1 sets the drive current flowing through the light-emitting element 131, that is, the current output from the constant current source 119 as an initial current in the setting state of a target drive current for the light-emitting element 131.

The operation of the ultraviolet-emitting device 1 will be described below with reference to FIGS. 5 to 7 in conjunction with FIGS. 1 and 4. FIGS. 5 and 7 or FIGS. 6 and 7 represent the operations of the ultraviolet-emitting device 1 in time sequence in the order of operations. The time scales represented in FIGS. 5 to 7 are different from the actual scales. In addition, referring to FIGS. 5 and 6, the number of fluctuations in feedback voltage Vfb is not equal to the actual number of bits, and parts of the feedback voltage Vfb are simply indicated by straight arrows.

The ultraviolet-emitting device 1 is configured to operate in two states: the target value setting state in which a target drive current for the light-emitting element 131 is set and the sterilization operation state in which the object to be sterilized is sterilized by the light-emitting element 131. In the target value setting state, the ultraviolet-emitting device 1 sets a target value for the light-emitting element 131 (in the present embodiment, a target value for the amount of drive current for the light-emitting element 131) by executing four steps.

First, in the target value setting state, the initial value of the amplification factor of the amplifier 110 is set to a maximum value. The input bit value is set so that the initial value of the voltage output from the bias adjuster 111 is ½ of the maximum voltage VDD. The input bit value is further set so that the initial value of the voltage output from the offset adjuster 112 is ½ of the maximum voltage VDD. The state identification signal Smode is set to "1."

After the end of the above-mentioned initial setting, as illustrated in FIG. 5, at time t0, the operations of the setting circuit 11a and the auto power control circuit 11b are started without operating the light-emitting element 131. Since the light-emitting element 131 is inactive, no fluorescence is generated by the fluorescent glass element 22, but a dark current, for example, flows through the photodetection element 14, and the current is therefore input from the photodetection element 14 to the I/V conversion circuit 114. Since the amplification factor of the amplifier 110 is set to a maximum value, the feedback voltage Vfb is output from the addition unit 113. At time t1, the feedback voltage Vfb takes a value larger than the maximum voltage VDD.

When a feedback voltage Vfb having a value larger than the maximum voltage VDD is output from the addition unit 113, the microprocessor 116 reduces the amplification factor of the amplifier 110 in steps of one grade in the first step. The microprocessor 116 determines whether the feedback voltage Vfb has dropped to an input voltage VIN1 on the high side on which the operation of the microprocessor 116 is compensated for, every time the amplification factor of the amplifier 110 is reduced. The microprocessor 116 reduces the amplification factor of the amplifier 110 until it determines that the feedback voltage Vfb has dropped to the input voltage VIN1.

When the feedback voltage Vfb becomes lower than the input voltage VIN1 at, for example, time t2, in the second step the microprocessor 116 changes the input bit value in steps of one bit to lower the voltage output from the DAC for high-order bits provided in the offset adjuster 112. The microprocessor 116 determines whether the value of the feedback voltage Vfb falls within the range of ½ of the maximum voltage VDD to the error voltage (VDD/2+ΔV), every time the input bit value of the DAC for high-order bits is changed by one bit. When the microprocessor 116 determines that the value of the feedback voltage Vfb falls within the range of ½ of the maximum voltage VDD to the error voltage (VDD/2+ΔV) at, for example, time t3, it ends the change in input bit value of the DAC for high-order bits in the offset adjuster 112.

The ultraviolet-emitting device 1 executes the first and second steps again to adjust the offset voltage by the DAC for low-order bits provided in the offset adjuster 112. At time t3, the light-emitting element management circuit 11 sets the amplification factor of the amplifier 110 to a maximum value again. Thus, at time t4, the feedback voltage Vfb takes a value larger than the maximum voltage VDD.

When a feedback voltage Vfb having a value larger than the maximum voltage VDD is output from the addition unit 113, in the first step the light-emitting element management circuit 11 gradually reduces the amplification factor of the amplifier 110 to lower the feedback voltage Vfb to the input voltage VIN1 on the high side on which the operation of the microprocessor 116 is compensated for.

When the feedback voltage Vfb becomes lower than the input voltage VIN1 at, for example, time t5, in the second step the light-emitting element management circuit 11 changes the input bit value to lower the voltage output from the DAC for low-order bits provided in the offset adjuster 112. When the value of the feedback voltage Vfb falls within the range of ½ of the maximum voltage VDD to the error voltage (VDD/2+ΔV) at time t6, the light-emitting element management circuit 11 ends the change in input bit value of the DAC for low-order bits in the offset adjuster 112.

FIG. 5 illustrates an example in which the feedback voltage Vfb takes a value larger than the maximum voltage VDD when the operations of the setting circuit 11a and the auto power control circuit 11b are started in the target value setting state, but the feedback voltage Vfb may take a value smaller than the minimum voltage (0 V).

As illustrated in FIG. 6, at time t0, the operations of the setting circuit 11a and the auto power control circuit 11b are started without operating the light-emitting element 131. Since the light-emitting element 131 is inactive, no fluorescence is generated by the fluorescent glass element 22, but a dark current, for example, flows through the photodetection element 14, and the current is therefore input from the photodetection element 14 to the I/V conversion circuit 114. Since the amplification factor of the amplifier 110 is set to a maximum value, the feedback voltage Vfb is output from the addition unit 113. At time t1, the feedback voltage Vfb takes a value smaller than the minimum voltage (0 V).

When a feedback voltage Vfb having a value smaller than the minimum voltage (0 V) is output from the addition unit 113, in the first step the light-emitting element management circuit 11 gradually reduces the amplification factor of the amplifier 110 to raise the feedback voltage Vfb to an input voltage VIN2 on the low side on which the operation of the microprocessor 116 is compensated for.

When the feedback voltage Vfb becomes higher than the input voltage VIN2 at, for example, time t2, in the second step the microprocessor 116 changes the input bit value in steps of one bit to raise the voltage output from the DAC for high-order bits provided in the offset adjuster 112. When the microprocessor 116 determines that the value of the feedback voltage Vfb falls within the range of ½ of the maximum voltage VDD to the error voltage (VDD/2−ΔV) at time t3, it ends the change in input bit value of the DAC for high-order bits in the offset adjuster 112.

The ultraviolet-emitting device 1 executes the first and second steps again to adjust the offset voltage by the DAC for low-order bits provided in the offset adjuster 112. At time t3, the light-emitting element management circuit 11 sets the amplification factor of the amplifier 110 to a maximum value again. Thus, at time t4, the feedback voltage Vfb takes a value smaller than the minimum voltage (0 V).

When a feedback voltage Vfb having a value smaller than the minimum voltage (0 V) is output from the addition unit 113, in the first step the microprocessor 116 reduces the amplification factor of the amplifier 110 in steps of one grade to raise the feedback voltage Vfb to the input voltage VIN2 on the low side on which the operation of the microprocessor 116 is compensated for.

When the feedback voltage Vfb becomes higher than the input voltage VIN2 at, for example, time t5, in the second step the microprocessor 116 changes the input bit value in steps of one bit to raise the voltage output from the DAC for low-order bits provided in the offset adjuster 112. When the value of the feedback voltage Vfb falls within the range of ½ of the maximum voltage VDD to the error voltage (VDD/2−ΔV) at time t6, the change in input bit value of the DAC for low-order bits in the offset adjuster 112 is ended.

Periods P1 and P3 illustrated in FIGS. 5 and 6 correspond to the first step in which the amplification factor of the amplifier 110 is adjusted. Periods P2 and P4 illustrated in FIGS. 5 and 6 correspond to the second step in which an offset voltage included in the entire circuit constituting the ultraviolet-emitting device 1 is adjusted using the offset adjuster 112.

While the amplification factor of the amplifier 110 and the input bit values of the bias adjuster 111 and the offset adjuster 112 in the target value setting state are kept the same as in the state in which the second step has ended twice, a current having an initial value is supplied to the light-emitting element 131 at time t7. With this operation, the light-emitting element 131 starts its operation to emit ultraviolet rays. Since the fluorescent glass element 22 emits fluorescence upon being excited by ultraviolet rays incident from the light-emitting element 131, a current is input from the photodetection element 14 to the I/V conversion circuit 114. The current flowing from the photodetection element 14 to the I/V conversion circuit 114 in this case is larger than the amount of dark current by several orders of magnitude. Accordingly, at time t8, the feedback voltage Vfb output from the addition unit 113 takes a value larger than the maximum voltage VDD.

When a feedback voltage Vfb having a value larger than the maximum voltage VDD is output from the addition unit 113, in the third step the microprocessor 116 reduces the amplification factor of the amplifier 110 in steps of one grade to lower the feedback voltage Vfb to the input voltage VIN1 on the high side on which the operation of the microprocessor 116 is compensated for.

When the feedback voltage Vfb becomes lower than the input voltage VIN1 at, for example, time t9, in the fourth step the microprocessor 116 changes the input bit value in steps of one bit to lower the voltage output from the DAC provided in the bias adjuster 111. When the value of the feedback voltage Vfb falls within the range of ½ of the maximum voltage VDD to the error voltage (VDD/2+ΔV) at time t10, the change in input bit value of the DAC in the bias adjuster 111 is ended. The microprocessor 116 stores a digital signal, obtained by A/D-converting the feedback voltage Vfb at time t10 by the A/D converter 115, in a predetermined storage area as a target code. The microprocessor 116 sets an upper limit threshold code and a lower limit threshold code in a predetermined storage area, based on the stored target code. Thus, the ultraviolet-emitting device 1 completes the initial setting operation.

A period P5 illustrated in FIG. 7 corresponds to the third step in which the amplification factor of the amplifier 110 is adjusted when a current having an initial value has been supplied to the light-emitting element 131. A period P6 illustrated in FIG. 7 corresponds to the fourth step in which a DC bias included in the feedback voltage Vfb is adjusted when a current having an initial value has been supplied to the light-emitting element 131.

When the ultraviolet-emitting device 1 completes the initial setting operation, it sets the state identification signal Smode to "0." When the sterilization module M1 starts to sterilize the object to be sterilized at subsequent time t11, and the light-emitting element 131 continues to emit light, the light-emitting element 131 deteriorates over time and voltage vs. current characteristic of the light-emitting element 121 varies. Thus, at time t12, the feedback voltage Vfb becomes lower than a lower limit threshold voltage VthL corresponding to the lower limit threshold code.

The microprocessor 116 determines that the value of the digital signal input from the A/D converter 115 is smaller than the lower limit threshold code and the light-emitting element 131 maintains no desired emission intensity. Therefore, the microprocessor 116 outputs an instruction signal for increasing the drive current for the light-emitting element 131 to the PWM signal generator 117. Upon receiving the instruction signal, the PWM signal generator 117 generates a duty signal Sduty higher in duty ratio than the duty signal Sduty corresponding to the target code and outputs it to the light-emitting element driving circuit 11c. As a result, since the amount of current output from the constant current source 119 increases, the current flowing through the light-emitting element 131 also increases.

By repeating an operation for changing the duty ratio of the duty signal Sduty in the auto power control circuit 10, the amount of drive current flowing through the light-emitting element 131 increases, and the emission intensity returns to a desired intensity at, for example, time t13. Since the feedback voltage Vfb thus exceeds ½ of the maximum voltage VDD, the microprocessor 116 determines that the value of the digital signal input from the A/D converter 115 falls within the range of the upper limit threshold code and the lower limit threshold code, and the light-emitting element 131 maintains a desired emission intensity. Then, the microprocessor 116 stops outputting an instruction signal for increasing the drive current for the light-emitting element 131 to the PWM signal generator 117. The PWM signal generator 117 thus continuously outputs a duty signal Sduty having the last output duty ratio to the light-emitting element driving circuit 11c. As a result, the amount of current output from the constant current source 119 is maintained, and the amount of current flowing through the light-emitting element 131 is also maintained. The light-emitting element 131 maintains a desired emission intensity accordingly. In this manner, in the ultraviolet-emitting device 1, the microprocessor 116 can detect and compensate for the deterioration over time of the light-emitting element 131.

Assume that the feedback voltage Vfb becomes lower than the lower limit threshold voltage VthL at, for example, time t14, after time t13, upon continuation of the operation of the sterilization module M1. Then, the ultraviolet-emitting device 1 performs the same operation as that at time t12 to time t13. As a result, at time t15, the feedback voltage Vfb exceeds ½ of the maximum voltage VDD and the light-emitting element 131 emits light with a desired emission intensity again.

The ultraviolet-emitting device 1 performs initial setting of an operating point for the light-emitting element 131 to obtain not the maximum emission intensity of the light-emitting element 131 but a minimum emission intensity required to sterilize the object to be sterilized. Therefore, the ultraviolet-emitting device 1 can repeatedly compensate for the operation of the light-emitting element 131 until the operating point after compensation reaches an operating point having a maximum emission intensity even when the deterioration over time occurs in the light-emitting element 131.

The ultraviolet-emitting device 1 adjusts the offset voltage of the entire circuit constituting the ultraviolet-emitting device 1 in the target value setting state to set the feedback voltage Vfb to ½ of the maximum voltage VDD. Hence, even when the voltage fluctuates in the sterilization operation state, it is hardly probable that the feedback voltage Vfb will be higher than the maximum voltage VDD or lower than the minimum voltage (0 V). As a result, the ultraviolet-emitting device 1 can stabilize the sterilization operation in the sterilization module M1.

Assume that, after the operation of the light-emitting element 131 is started (after time t11 in FIG. 7), the lid portion 312 of the sterilization module M1 is opened, although not illustrated. Then, not only fluorescence emitted by the fluorescent glass element 22 but also external light strikes the photodetection element 14. The amount of external light is larger than the amount of fluorescence emitted by the fluorescent glass element 22 by several orders of magnitude. The feedback voltage Vfb is therefore higher than the maximum voltage VDD. Before the start of the operation of the light-emitting element 131, the microprocessor 116 receives a state identification signal Smode having value "0." The light-emitting element management circuit 11 stops the operation of the light-emitting element 131 by, for example, forcibly setting the value of the feedback voltage Vfb input to the A/D converter 115 to 0V or inputting a duty signal Sduty having zero duty ratio to the controller 118 of the light-emitting element driving circuit 11c. Hence, the ultraviolet-emitting device 1 can prevent ultraviolet rays from leaking out of the accommodation member 31.

As described above, the ultraviolet-emitting device 2 according to the present embodiment includes alight-emitting element 131 which emits ultraviolet rays, a mounting board 314 on which the light-emitting element 131 is placed, a fluorescent glass element 22 placed at a position irradiated with the ultraviolet rays emitted by the light-emitting element 131, and placed in a through hole 314a formed through the mounting board 314, and emitting fluorescence in the visible range by excitation of an ultraviolet rays, and a photodetection element 14 which detects the intensity of the fluorescence emitted by the fluorescent glass element 22. Hence, the ultraviolet-emitting device 2 achieves prolonged life of the light-emitting element 131 while maintaining a certain emission intensity of the light-emitting element 131.

The ultraviolet-emitting device 2 further includes electronic components (for example, a light-emitting element management circuit 11) on the opposite side of the placement side of the light-emitting element 131 is placed with respect to the mounting board 314. Hence, the ultraviolet-emitting device 2 can prevent the light-emitting element management circuit 11 that controls the light-emitting element 131 from being deteriorated by ultraviolet rays emitted by the light-emitting element 131.

The ultraviolet-emitting device 2 can automatically learn the initial value of the drive current for the light-emitting element 131 within the range of variation in the circuit system constituting the ultraviolet-emitting device 2 and operate to maintain the emission intensity (output power) of the light-emitting element 131 constant when the deterioration over time of the light-emitting element 131 falls within the expected range.

The ultraviolet-emitting device 2 can stop the light-emitting element 131 when a high power exceeding the gain of the circuit system constituting the ultraviolet-emitting device 2 is input (that is, when the lid portion 312 of the sterilization module M2 is opened during a sterilization operation). Hence, the ultraviolet-emitting device 2 can serve as a safety device.

The ultraviolet-emitting device 2 uses the fluorescent glass element 22 to keep ultraviolet rays from being directly input to the photodetection element 14. This can prevent the resin used to mold the detection unit of the photodetection element 14 from deteriorating upon irradiation with ultraviolet rays. Since the feedback voltage Vfb can hardly include variations based on the deterioration of the photodetection element 14, the deterioration of the light-emitting element 131 can be accurately compensated for based on the feedback voltage Vfb.

The ultraviolet-emitting device 2 can use the fluorescent glass element 22 to convert 265-nm-wavelength ultraviolet rays emitted by the light-emitting element 131 into 580-nm-wavelength fluorescence and detect the ultraviolet rays emitted by the light-emitting element 131. This allows the use of a highly sensitive photodetection element 14 and, in turn, allows stabilization of the operation of the light-emitting element management circuit 11.

Embodiment 2-2

An ultraviolet-emitting device according to Embodiment 2-2 of the present invention will be described below with reference to FIG. 10. An ultraviolet-emitting device 3 according to the present embodiment and a sterilization module M3 including the ultraviolet-emitting device 3 are the same as the ultraviolet-emitting device 2 according to above-described Embodiment 2-1 and the sterilization module M2 including the ultraviolet-emitting device 2, except that the former includes a reflecting member. Therefore, in the ultraviolet-emitting device 3 and the sterilization module M3, the same reference numerals denote components exhibiting the same actions and functions as those of the components constituting the ultraviolet-emitting device 2 and the sterilization module M2, and a description thereof will not be given.

Figure 10:
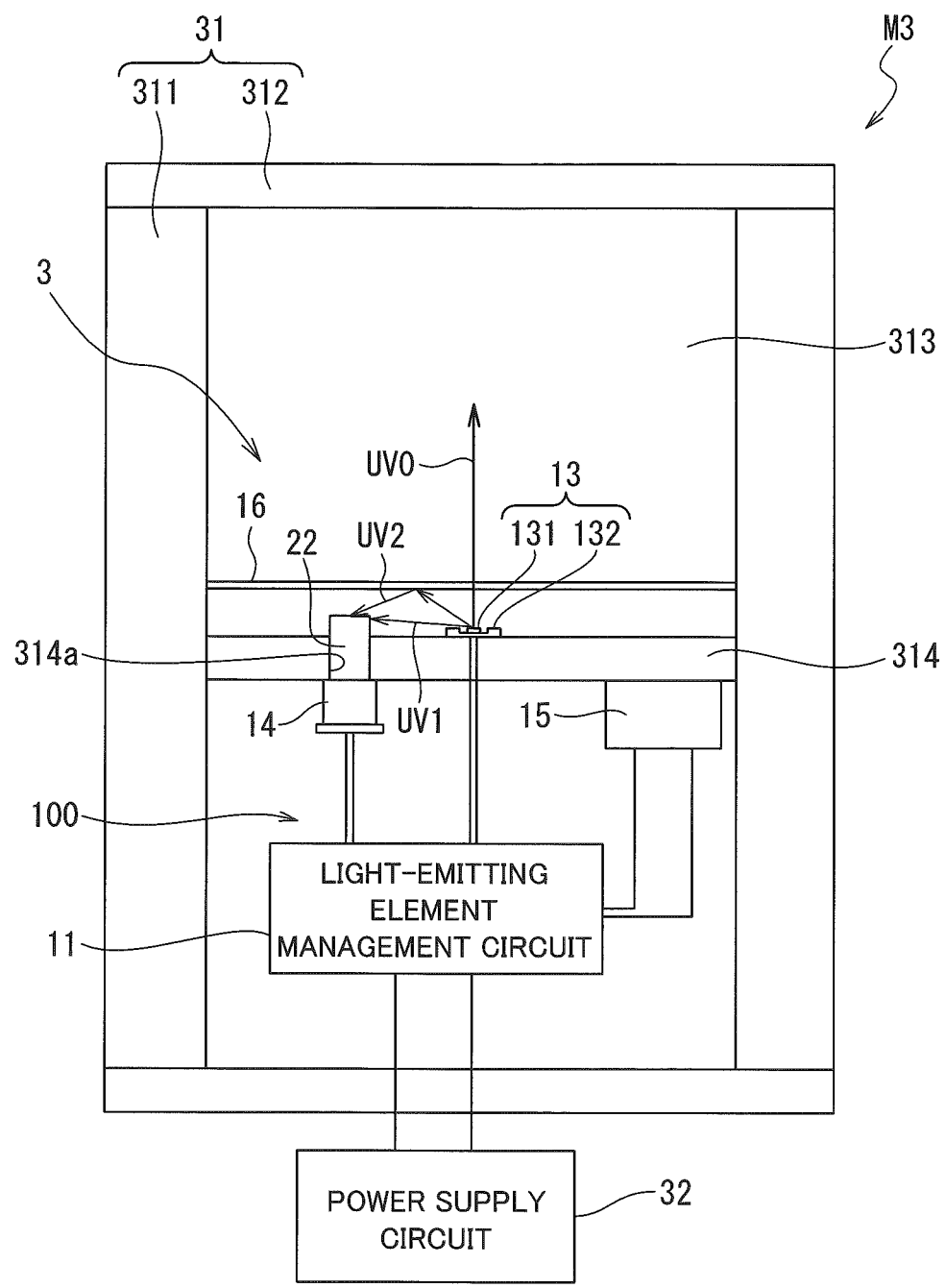
FIG. 10 is a diagram typically illustrating the schematic configuration of a sterilization module M3 including an ultraviolet-emitting device 3 according to Embodiment 2-2 of the present invention.

The ultraviolet-emitting device 3 includes a reflecting member 16 which reflects a part of ultraviolet rays emitted by a light-emitting element 131 and transmits a part of the remaining the ultraviolet rays, as illustrated in FIG. 10. The reflecting member 16 is made of a material which reflects a very minor part (for example, less than 5% of incident light) of incident ultraviolet rays and transmits the remaining major part of the ultraviolet rays. The reflecting member 16 is made of, for example, glass. A fluorescent glass element 22 protrudes from a mounting board 314 to a level higher than the light-emitting element 131. With this arrangement, the fluorescent glass element 22 receives not only ultraviolet rays UV1 as direct light emitted by the light-emitting element 131 but also ultraviolet rays UV2 reflected by the reflecting member 16. Therefore, the fluorescent glass element 22 receives ultraviolet rays in an amount larger than ultraviolet rays incident on the fluorescent glass element 22 in above-described Embodiment 2-1 by the amount of ultraviolet rays UV2 reflected by the reflecting member 16. As a result, the fluorescent glass element 22 emits fluorescence with a higher intensity, leading to a higher detection sensitivity of a photodetection element 14.

An accommodation space 313 is surrounded by a main body portion 311, a lid portion 312, and the reflecting member 16. An object (not illustrated) to be sterilized accommodated in the accommodation space 313 is sterilized with ultraviolet rays UV0 emitted by the light-emitting element 131 and transmitted through the reflecting member 16. As described above, ultraviolet rays are reflected by the reflecting member 16 in an amount as very small as, for example, less than 5% of the amount of ultraviolet rays incident on the reflecting member 16. Therefore, even when the ultraviolet-emitting device 3 includes the reflecting member 16, it can guide the ultraviolet rays UV0 to the accommodation space 313 in an amount which allows sufficient sterilization of the object to be sterilized accommodated in the accommodation space 313. Hence, since the ultraviolet-emitting device 3 can guide ultraviolet rays emitted by the light-emitting element 131 to the fluorescent glass element 22 and efficiently guide them to the object to be sterilized accommodated in the accommodation space 313, the sterilization module M3 can prevent degradation in sterilization efficiency of the object to be sterilized.

The fluorescent glass element 22 may have one end face inclined in two steps and exposed on the element mounting surface of the mounting board 314 to allow nearly perpendicular incidence of the ultraviolet rays UV1 and UV2.

Since the operation of the ultraviolet-emitting device 3 according to the present embodiment is the same as that of the ultraviolet-emitting device 2 according to above-described Embodiment 2-1, a description thereof will not be given.

As described above, the ultraviolet-emitting device 3 according to the present embodiment includes alight-emitting element 131 which emits ultraviolet rays, a mounting board 314 on which the light-emitting element 131 is placed, and a fluorescent glass element 22 placed at a position irradiated with the ultraviolet rays emitted by the light-emitting element 131, and placed in a through hole 314*a* formed through the mounting board 314, and emitting fluorescence in the visible range by excitation of an ultraviolet rays. Hence, the ultraviolet-emitting device 3 has the same effect as the ultraviolet-emitting device 2 according to above-described Embodiment 2-1.

The ultraviolet-emitting device 3 further includes electronic components (for example, a light-emitting element management circuit 11) on the opposite side of the placement side of the light-emitting element 131 with respect to the mounting board 314. Hence, the ultraviolet-emitting device 3 has the same effect as the ultraviolet-emitting device 2 according to above-described Embodiment 2-1.

The ultraviolet-emitting device 3 further includes a reflecting member 16 which reflects a part of ultraviolet rays emitted by the light-emitting element 131 and transmits a part of the remaining the ultraviolet rays. With this arrangement, the fluorescent glass element 22 receives not only ultraviolet rays UV1 as direct light emitted by the light-emitting element 131 but also ultraviolet rays UV2 reflected by the reflecting member 16. As a result, compared to above-described Embodiment 2-1, since ultraviolet rays are applied to the fluorescent glass element 22 in a larger amount, the fluorescent glass element 22 emits fluorescence with a higher intensity, leading to a higher detection sensitivity of the photodetection element 14.

Embodiment 2-3

Figure 11A:
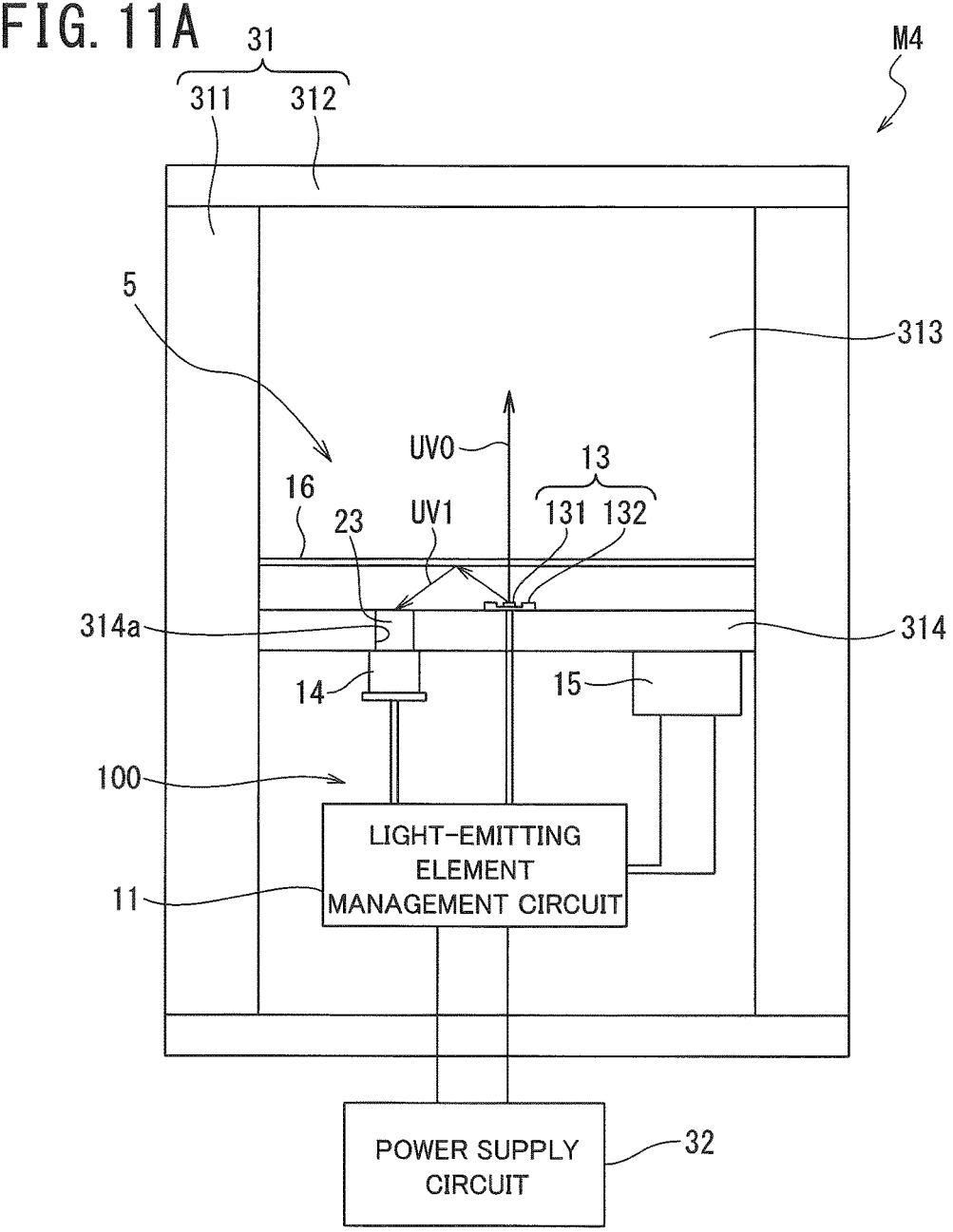
FIG. 11A is a diagram typically illustrating the schematic configuration of a sterilization module M4 including an ultraviolet-emitting device 4.

An ultraviolet-emitting device according to Embodiment 2-3 of the present invention will be described below with reference to FIG. 11. An ultraviolet-emitting device 4 according to the present embodiment and a sterilization module M4 including the ultraviolet-emitting device 4 are the same as the ultraviolet-emitting device 3 according to above-described Embodiment 2-2 and the sterilization module M3 including the ultraviolet-emitting device 3, except that the former includes a fluorescent glass element placed without protruding from a board to a level higher than a light-emitting element. Therefore, in the ultraviolet-emitting device 4 and the sterilization module M4, the same reference numerals denote components exhibiting the same actions and functions as those of the components constituting the ultraviolet-emitting device 3 and the sterilization module M3, and a description thereof will not be given.

A fluorescent glass element 23 is inserted into the through hole 314*a* and is disposed through a mounting board 314, as illustrated in FIG. 11. The fluorescent glass element 23 is partially exposed on the element mounting surface of the mounting board 314. With this arrangement, ultraviolet rays UV1 reflected by a reflecting member 16 can be guided to the fluorescent glass element 23. The fluorescent glass element 23 is also partially exposed on the mounting back surface of the mounting board 314. With this arrangement, the fluorescent glass element 23 can guide fluorescence in the visible range emitted by excitation of the ultraviolet rays UV1 to a photodetection element 14 placed below the mounting back surface of the mounting board 314. The fluorescent glass element 23 is partially exposed on the element mounting surface of the mounting board 314 and is therefore partially exposed on the side where a light-emitting element 131 is placed. Accordingly, the fluorescent glass element 23 corresponds to neither an electronic component on the opposite side of the placement side of the light-emitting element 131 with respect to the mounting board 314 nor an electronic component constituting an electronic component group 100.

Figure 11B:
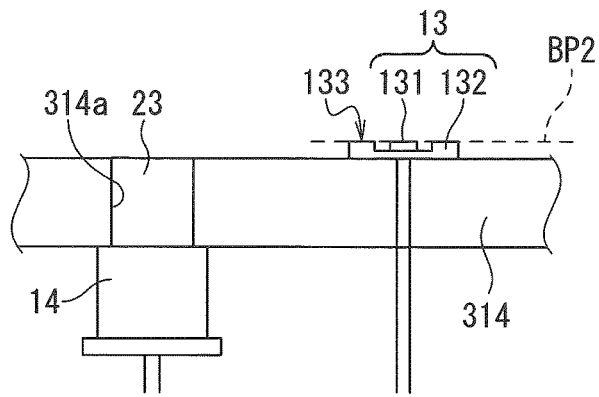
FIG. 11B is a schematic enlarged view illustrating a fluorescent glass element 23 and a light-emitting element 131 and their vicinity.

The fluorescent glass element 23 is placed with its one end face flush with the element mounting surface of the mounting board 314 at the position adjacent to the light-emitting element 131, as illustrated in FIG. 11B. More specifically, the fluorescent glass element 23 is located below the light-emitting element 131 with respect to an upper surface 133 of a ceramic package 132 accommodating the light-emitting element 131 and is adjacent to the light-emitting element 131 or adjacent to a light source 13. The "upper surface" may be defined herein, for example, as the surface of the ceramic package 132 opposite to a surface (that is, the element mounting surface) which allows the ceramic package 132 to come into contact with the mounting board 314, or as a virtual plane BP2 including this surface of the ceramic package 132.

By placing the fluorescent glass element 23 so as not to protrude from the light-emitting element 131 and the element mounting surface of the mounting board 314, the degree of freedom in designing the ultraviolet-emitting device 4 improves. By placing the fluorescent glass element 23 adjacent to the light-emitting element 131 keeps the fluorescent glass element 23 from crossing the optical axis of ultraviolet rays emitted by the light-emitting element 131. In other words, the fluorescent glass element 23 is not placed on ultraviolet rays UV0 having a highest intensity emitted by the light-emitting element 131 (see FIG. 11A). The light-emitting element 131 emits ultraviolet rays having a distribution of luminous intensity (see FIG. 2) similar to the Lambert distribution of luminous intensity and possesses a predetermined directivity. The ultraviolet-emitting device 4 is configured to irradiate the fluorescent glass element 23 with ultraviolet rays UV1 output not onto the optical axis of ultraviolet rays emitted by the light-emitting element 131 but at a predetermined angle with respect to the optical axis and reflected by a reflecting member 16. With this arrangement, the ultraviolet-emitting device 4 can guide the ultraviolet rays UV1 emitted by the light-emitting element 131 to a fluorescent glass element 22 while suppressing attenuation of the ultraviolet rays UV0 impinging on the object to be sterilized. Hence, the sterilization module M4 can prevent degradation in sterilization efficiency of the object to be sterilized.

The fluorescent glass element 23 has, for example, a quadrangular prismatic shape. The fluorescent glass element 23 has the same shape as that of the fluorescent glass element 22 except for the dimension in the direction of thickness of the mounting board 314. The shape of the fluorescent glass element 23 is not limited to this and may be prismatic shapes other than a quadrangular prismatic shape, circular and elliptical shapes and the like. The fluorescent glass element 23 may have its one end face inclined and exposed on the element mounting surface of the mounting board 314 to allow nearly perpendicular incidence of the ultraviolet rays UV1.

Since the operation of the ultraviolet-emitting device 4 according to the present embodiment is the same as that of the ultraviolet-emitting device 2 according to above-described Embodiment 2-1, a description thereof will not be given.

As described above, the ultraviolet-emitting device 4 according to the present embodiment includes alight-emitting element 131 which emits ultraviolet rays, a mounting board 314 on which the light-emitting element 131 is placed, and a fluorescent glass element 23 placed at a position irradiated with the ultraviolet rays emitted by the light-emitting element 131, and placed in a through hole 314a formed through the mounting board 314, and emitting fluorescence in the visible range by excitation of an ultraviolet rays. The ultraviolet-emitting device 4 further includes a reflecting member 16 which reflects a part of ultraviolet rays emitted by the light-emitting element 131 and transmits a part of the remaining the ultraviolet rays. Hence, the ultraviolet-emitting device 4 has the same effect as the ultraviolet-emitting device 3 according to above-described Embodiment 2-2.

The ultraviolet-emitting device 4 further includes electronic components (for example, a light-emitting element management circuit 11) on the opposite side of the placement side of the light-emitting element 131 with respect to the mounting board 314. Hence, the ultraviolet-emitting device 4 has the same effect as the ultraviolet-emitting device 2 according to above-described Embodiment 2-1.

The fluorescent glass element 23 provided in the ultraviolet-emitting device 4 is placed so as not to protrude from the light-emitting element 131 and the element mounting surface of the mounting board 314. This can improve the degree of freedom in designing the ultraviolet-emitting device 4.

Modifications to Embodiments 1 and 2

Ultraviolet-emitting devices according to modifications to Embodiments 1 and 2 will be described below with reference to FIG. 12. The ultraviolet-emitting devices according to the present modification have the same configurations as those of the ultraviolet-emitting device according to Embodiment 1 and the ultraviolet-emitting devices according to Embodiment 2, except for the shapes of fluorescent glass elements. Therefore, components other than the fluorescent glass elements for the ultraviolet-emitting devices according to the present modification will not be described.

Figure 12A:
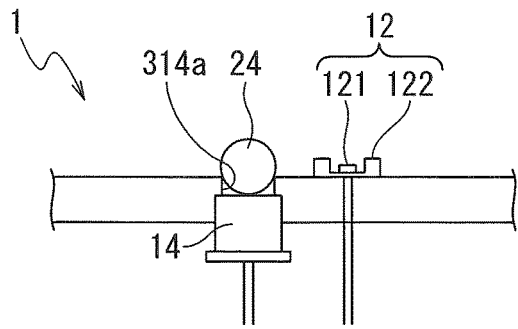
FIG. 12A is a diagram illustrating the main part of the schematic configuration of an ultraviolet-emitting device 1 according to the modification to Embodiment 1.

The ultraviolet-emitting device 1 according to the modification to Embodiment 1 includes a fluorescent glass element 24 having a spherical surface, as illustrated in FIG. 12A. The fluorescent glass element 24 has is a spherical shape. The surface of the fluorescent glass element 24 is formed in a spherical shape. The fluorescent glass element 24 is placed so as to protrude higher than the light-emitting element 121 at a position irradiated with ultraviolet rays emitted by the light-emitting element 121. The fluorescent glass element 24 is also placed on the photodetection element 14. Hence, the ultraviolet-emitting device 1 according to the present modification has the same effect as the ultraviolet-emitting device 1 according to Embodiment 1.

Figure 12B:
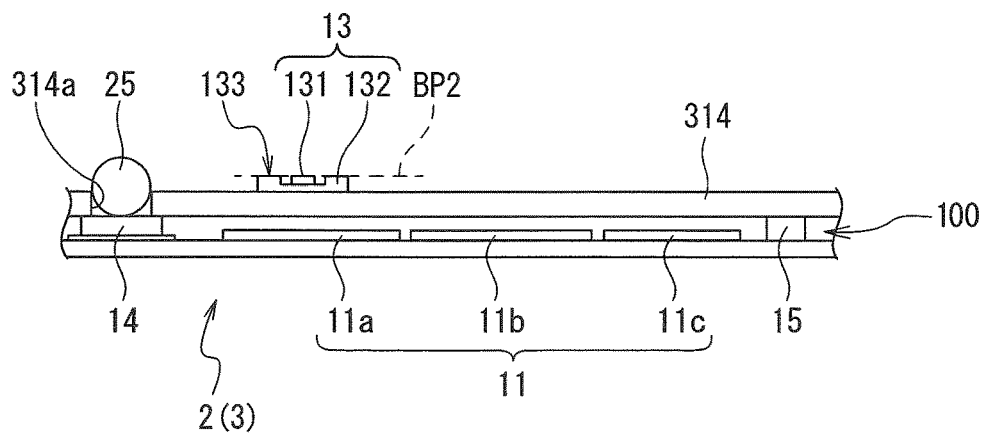
FIG. 12B is a diagram illustrating the main part of the schematic configuration of each of ultraviolet-emitting devices 2 and 3 according to the modifications to Embodiments 2-1 and 2-2.

The ultraviolet-emitting device 2 according to the modification to Embodiment 2-1 includes a fluorescent glass element 25 having a spherical surface, as illustrated in FIG. 12B. The fluorescent glass element 25 has a spherical shape. The surface of the fluorescent glass element 25 is formed in a spherical shape. The fluorescent glass element 25 is placed so as to protrude higher than the light-emitting element 131 at a position irradiated with ultraviolet rays emitted by the light-emitting element 131. The fluorescent glass element 25 is also placed at a position irradiated with ultraviolet rays emitted by the light-emitting element 131, and placed in a through hole 314a formed through the mounting board 314. The fluorescent glass element 25 is inserted into the through hole 314a and is arranged through the mounting board 314. The fluorescent glass element 25 is even placed on the photodetection element 14. Hence, the ultraviolet-emitting device 2 according to the present modification has the same effect as the ultraviolet-emitting device 2 according to Embodiment 2-1.

The ultraviolet-emitting device 3 according to the modification to Embodiment 2-2 includes a fluorescent glass element 25 identical to that of the ultraviolet-emitting device 2 according to the modification to Embodiment 2-1, as illustrated in FIG. 12B. Hence, the ultraviolet-emitting device 3 according to the present modification has the same effect as the ultraviolet-emitting device 3 according to Embodiment 2-2.

Figure 12C:
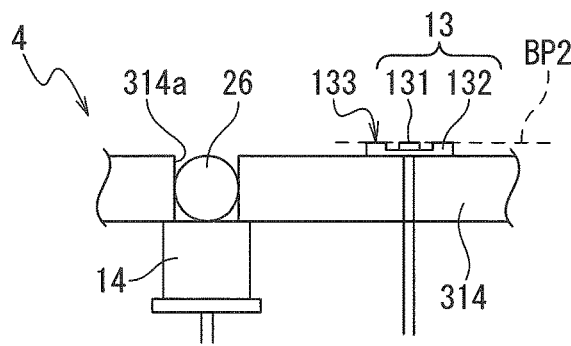
FIG. 12C is a diagram illustrating the main part of the schematic configuration of an ultraviolet-emitting device 4 according to the modification 1 to Embodiment 2-3.

The ultraviolet-emitting device 4 according to the modification 1 to Embodiment 2-3 includes a fluorescent glass element 26 having a spherical surface, as illustrated in FIG. 12C. The fluorescent glass element 26 has a spherical shape. The surface of the fluorescent glass element 26 is formed in a spherical shape. The fluorescent glass element 26 is placed at a position irradiated with ultraviolet rays emitted by the light-emitting element 131, and placed in a through hole 314a formed through the mounting board 314. The fluorescent glass element 26 is inserted into the through hole 314a and is arranged through the mounting board 314. The fluorescent glass element 26 is placed in the through hole 314*a* so that a mounting surface of the mounting board 314 on which the light source 13 is mounted and an apex of the fluorescent glass element 26 exposed in the through hole 314*a* are flush with each other. The fluorescent glass element 26 may be placed in the through hole 314*a* so that the apex exposed in the through hole 314*a* is lower than the mounting surface of the mounting board 314. The fluorescent glass element 26 is also placed on the photodetection element 14. The fluorescent glass element 26 is even placed lower than the upper surface 133 of the ceramic package 132 of the light source 13. This makes it hard for ultraviolet rays emitted by the light-emitting element 131 to directly strike the fluorescent glass element 26. However, the ultraviolet-emitting device 4 according to the present modification includes a reflecting member 16 (not illustrated in FIG. 12C; see FIG. 11A) above the light source 13, like the ultraviolet-emitting device 4 according to Embodiment 2-3. Hence, since ultraviolet rays reflected by the reflecting member 16 are applied to the fluorescent glass element 26, the ultraviolet-emitting device 4 according to the present modification has the same effect as the ultraviolet-emitting device 4 according to Embodiment 2-3.

Figure 12D:
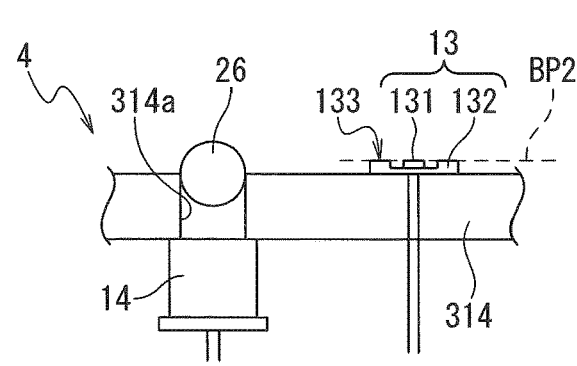
FIG. 12D is a diagram illustrating the main part of the schematic configuration of an ultraviolet-emitting device 4 according to the modification 2 to Embodiment 2-3.

The ultraviolet-emitting device 4 according to the modification 2 to Embodiment 2-3 includes a fluorescent glass element 26 having a spherical surface, like the ultraviolet-emitting device 4 according to the modification 1, as illustrated in FIG. 12D. However, in the ultraviolet light emitting device 4 according to the present modification the fluorescent glass element 26 is inserted into the through hole 314*a* so that a part of the fluorescent glass element 26 is higher than the mounting surface of the mounting board 314, unlike the ultraviolet light emitting device 4 according to the modification 1. Also in the ultraviolet light emitting device 4 according to present modification, a part of the ultraviolet rays emitted by the light source 13 is reflected by the reflecting member 16 and is irradiated to the fluorescent glass element 26. Hence, the ultraviolet-emitting device 4 according to the present modification has the same effect as the ultraviolet-emitting device 4 according to the Embodiment 2-3. The ultraviolet-emitting device 4 according to the present modification can guide directly a part of the ultraviolet rays emitted by the light source 13 to the fluorescent glass element 26. Hence, the ultraviolet-emitting device 4 according to the present modification can improve the detection sensitivity of ultraviolet rays more than the ultraviolet-emitting device 4 according to the Embodiment 2-3.

Figure 12E:
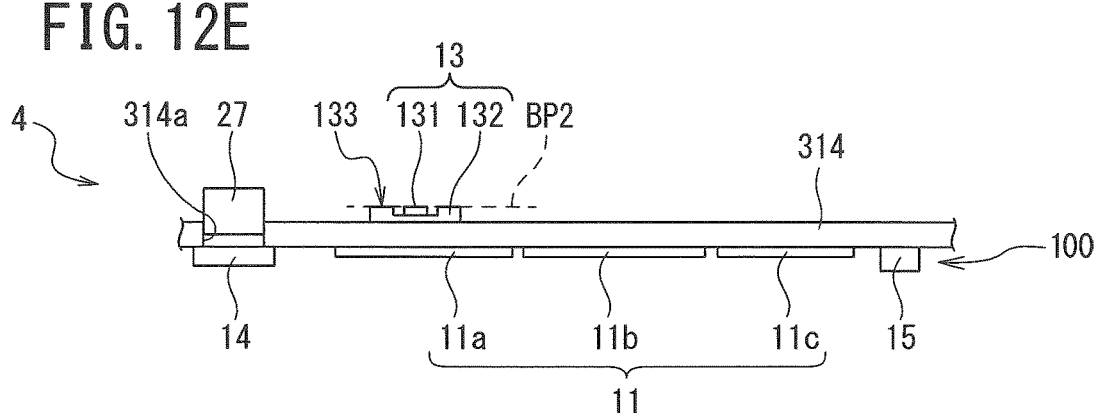
FIG. 12E is a diagram illustrating the main part of the schematic configuration of an ultraviolet-emitting device 4 according to the modification 3 to Embodiment 2-3.

The ultraviolet-emitting device 4 according to the modification 3 to Embodiment 2-3 includes a fluorescent glass element 27 having a rectangular parallelepiped shape, unlike the ultraviolet-emitting device 4 according to the modification 2, as illustrated in FIG. 12E. In the present modification, the fluorescent glass element 27 has the rectangular parallelepiped shape, but may have a cubic shape. The fluorescent glass element 27 is inserted into the through hole 314*a* so that a part of the fluorescent glass element 27 is higher than the mounting surface of the mounting board 314. Also in the ultraviolet light emitting device 4 according to present modification, the ultraviolet rays emitted by the light source 13 is reflected by the reflecting member 16 and is irradiated to the fluorescent glass element 27. Hence, the ultraviolet-emitting device 4 according to the present modification has the same effect as the ultraviolet-emitting device 4 according to the Embodiment 2-3. The ultraviolet-emitting device 4 according to the present modification can guide directly a part of the ultraviolet rays emitted by the light source 13 to the fluorescent glass element 27. Hence, the ultraviolet-emitting device 4 according to the present modification can improve the detection sensitivity of ultraviolet rays more than the ultraviolet-emitting device 4 according to the Embodiment 2-3.

Further, as shown in FIG. 12E, the ultraviolet-emitting device 4 according to the present modification has a photodetection element 14, the light-emitting element management circuit 11, and a temperature sensor 15 and the like on the back surface of the mounting surface of the mounting board 314 on which the light source 13 is mounted. Hence, even when the mounting board 314 has a configuration capable of double-sided mounting, it is possible to prevent the ultraviolet rays emitted by the light source 13 from being irradiated to the photodetection element 14, the light-emitting element management circuit 11, and the temperature sensor 15. Thereby, the ultraviolet-emitting device 4 according to the present modification can prevent the electronic component group from being deteriorated by the ultraviolet light emitted by the light source 13.

The present invention is not limited to the above-described embodiments, and various modifications may be made.

The light-emitting element management circuit 11 provided in each of the ultraviolet-emitting device 1 according to the Embodiment 1 and the ultraviolet-emitting devices 2, 3, 4 according to the Embodiment 2 can control the light emitting element 121 or 131 so as to maintain the desired light emitting intensity by feeding back the emission intensity of the light-emitting element 121 or 131 during a sterilization operation for the object to be sterilized by the light-emitting element 121 or 131, but the present invention is not limited to this. The light-emitting element management circuit 11 may detect an output based on the intensity of the fluorescence detected by the photodetection element 14 and monitor the light amount of the light emitting element 121 or 131. That is, the management of the light emitting element 121 or 131 by the light-emitting element management circuit 11 may be either feedback control of the light emission intensity of the light emitting element 121 or 131 described above or monitoring of the light amount of the light emitting element 121 or 131 described above. Further, as the management of the light emitting element 121 or 131, the light-emitting element management circuit 11 may perform both feedback control of the light emission intensity of the light emitting element 121 or 131 described above and monitoring of the light amount of the light emitting element 121 or 131 described above.

The ultraviolet-emitting device 1 according to above-described Embodiment 1 and the ultraviolet-emitting devices 2, 3, and 4 according to above-described Embodiment 2 include the offset adjusters 112, but the present invention is not limited to this. For example, the ultraviolet-emitting devices 1, 2, 3, and 4 may include no offset adjusters 112. An ultraviolet-emitting device as in this case cannot adjust the value of the feedback voltage Vfb to ½ of the maximum voltage VDD in the target value setting state and are therefore less stable with respect to variations in voltage of the analog power supply, compared to the ultraviolet-emitting device 1 according to above-described Embodiment 1 and the ultraviolet-emitting devices 2, 3, and 4 according to above-described Embodiment 2. However, this ultraviolet-emitting device achieves simple circuitry and target value setting processing because it includes no offset adjuster.

In above-described Embodiments 1 and 2, the target value is defined as the drive current for the light-emitting element 121, but the present invention is not limited to this. The same effect can be obtained even when, for example, the target value is defined as the voltage applied to the light-emitting element 121 and the drive current takes a fixed value.

In above-described Embodiments 1 and 2, a generator which receives an instruction signal output from the microprocessor 116 is implemented as the pulse-width modulated signal generator 117, but the present invention is not limited to this. The generator may be implemented in, for example, a digital-to-analog conversion circuit.

In above-described Embodiments 1 and 2, an offset voltage generated by the entire circuit constituting each of the ultraviolet-emitting devices 1, 2, 3, and 4 is adjusted by adding or subtracting the voltage output from the offset adjuster 112 to or from that output from the amplifier 110, but the present invention is not limited to this. This offset voltage can be adjusted even by, for example, directly adding or subtracting a current to or from the I/V conversion circuit 114. In this case, the offset adjuster 112 can output a current according to the input value (the input bit value when the offset adjuster 112 is implemented in a DAC) to the I/V conversion circuit 114.

Each of the ultraviolet-emitting devices 2, 3, and 4 according to above-described Embodiments 2-1 to 2-3 includes a mounting board 314 made of a member absorbing or reflecting ultraviolet rays, but the present invention is not limited to this. A predetermined film absorbing or reflecting ultraviolet rays may be formed on the surface of the mounting board 314. Even in this case, since the mounting board 314 can prevent ultraviolet rays from striking the side opposite to the element mounting surface, the same effect as in the ultraviolet-emitting devices 2, 3, and 4 according to above-described Embodiments 2-1 to 2-3 can be obtained.

Apart of the mounting board 314 may be made of a member absorbing or reflecting ultraviolet rays, and the light-emitting element management circuit 11, for example, may be placed on the opposite side of the element mounting surface in the part of the mounting board 314. Alternatively, a predetermined film absorbing or reflecting ultraviolet rays may be formed on a part of the surface of the mounting board 314, and the light-emitting element management circuit 11, for example, may be placed on the opposite side of the element mounting surface including the predetermined film formed on it. Even in this case, since the mounting board 314 can prevent ultraviolet rays from striking the side opposite to the element mounting surface, the same effect as in the ultraviolet-emitting devices 2, 3, and 4 according to above-described Embodiments 2-1 to 2-3 can be obtained.

In above-described Embodiment 1 and Embodiments 2-1 to 2-3, the light-emitting element management circuit 11 may include a mechanism which receives a signal for driving the light-emitting element 121 (or the light-emitting element 131) from the outside or outputs a signal for sending the information of the emission state of the light-emitting element 121 (or the light-emitting element 131) or the state of the light-emitting element management circuit 11 to the outside.

Above-described Embodiment 1 and Embodiments 2-1 to 2-3 exemplify devices or operations for embodying the technical idea of the present invention, and the technical idea of the present invention does not limit, for example, the materials, shapes, structures, and arrangements of components to specific examples. Various changes can be made to the technical idea of the present invention within the technical scope defined by claims described in the scope of claims.

The light emitting element 121 in the Embodiment 1 is provided in a ceramic package 122, and the light emitting elements 131 in the Embodiments 2-1 to 2-3 and each of the Modifications are provided in the ceramic package 132, but the present invention is not limited to this. For example, the light emitting elements 121 and 131 may be provided in a package made of a material other than ceramic. The light emitting elements 121 and 131 may be directly mounted (for example, die mounted) on the mounting board 314 without having a package.

REFERENCE SIGNS LIST 1, 2, 3, 4 . . . ultraviolet-emitting device
11 . . . light-emitting element management circuit
11a . . . setting circuit
11b . . . auto power control circuit
11c . . . light-emitting element driving circuit
12 . . . light source
14 . . . photodetection element
15 . . . temperature sensor
16 . . . reflecting member
21, 22, 23, 26, 27 . . . fluorescent glass element
31 . . . accommodation member
32 . . . power supply circuit
100 . . . electronic component group
110 . . . amplifier
111 . . . bias adjuster
112 . . . offset adjuster
113 . . . addition unit
114 . . . current-to-voltage conversion circuit
115 . . . analog-to-digital converter
116 . . . microprocessor
117 . . . pulse-width modulated signal generator
118 . . . controller
119 . . . constant current source
121, 131 . . . light-emitting element
122, 132 . . . ceramic package
123, 133 . . . upper surface
211 . . . inclined surface
311 . . . main body portion
312 . . . lid portion
313 . . . accommodation space
314 . . . mounting board
M1, M2, M3 . . . sterilization module

The invention claimed is:

1. An ultraviolet-emitting device comprising:
an accommodation member having an accommodation space;
a light-emitting element configured to emit an ultraviolet ray into the accommodation space, the accommodation space being configured to accommodate therewithin the light-emitting element and an object to be sterilized;
a board in the accommodation space on which the light-emitting element is placed;
a fluorescent glass element placed at a position irradiated with the ultraviolet ray passing through the accommodation space, and placed in a through hole formed through the board, emitting fluorescence in a visible range by excitation of an ultraviolet ray; and
a photodetection element configured to detect an intensity of the fluorescence emitted by the fluorescent glass element.

2. The ultraviolet-emitting device according to claim 1, wherein the photodetection element is placed on an opposite side of a placement side of the light-emitting element with respect to the board.

3. The ultraviolet-emitting device according to claim 2, further comprising a reflecting member configured to reflect a part of the ultraviolet ray emitted by the light-emitting element and transmit a part of a remaining the ultraviolet ray,
  wherein the fluorescent glass element is placed at a position irradiated with the ultraviolet ray reflected by the reflecting member.

4. The ultraviolet-emitting device according to claim 2, wherein the fluorescent glass element is formed in a pillar shape and has, at one end, an inclined surface lower in a direction away from the light-emitting element.

5. The ultraviolet-emitting device according to claim 2, wherein the fluorescent glass element is formed in a shape having a spherical surface.

6. The ultraviolet-emitting device according to claim 2, further comprising a reflecting member configured to reflect a part of the ultraviolet ray emitted by the light-emitting element and transmit a part of a remaining the ultraviolet ray,
  wherein the fluorescent glass element is placed at a position irradiated with the ultraviolet ray reflected by the reflecting member.

7. The ultraviolet-emitting device according to claim 1, further comprising a reflecting member configured to reflect a part of the ultraviolet ray emitted by the light-emitting element and transmit a part of a remaining the ultraviolet ray,
  wherein the fluorescent glass element is placed at a position irradiated with the ultraviolet ray reflected by the reflecting member.

8. The ultraviolet-emitting device according to claim 1, wherein the fluorescent glass element is formed in a pillar shape and has, at one end, an inclined surface lower in a direction away from the light-emitting element.

9. The ultraviolet-emitting device according claim 1, wherein the fluorescent glass element is formed in a shape having a spherical surface.

10. The ultraviolet-emitting device according to claim 1, wherein the light-emitting element is provided to allow irradiation of the object to be sterilized with the ultraviolet ray.

11. An ultraviolet-emitting device comprising:
  an accommodation member having an accommodation space;
  a light-emitting element configured to emit an ultraviolet ray into the accommodation space, the accommodation space being configured to accommodate therewithin the light-emitting element and an object to be sterilized;
  a fluorescent glass element which is placed at a position, irradiated with the ultraviolet ray passing through the accommodation space, protruding higher than the light-emitting element, and emitting fluorescence in a visible range by excitation of an ultraviolet ray;
  a board on which the light-emitting element is placed; and
  a photodetection element configured to detect an intensity of the fluorescence emitted by the fluorescent glass element.

12. The ultraviolet-emitting device according to claim 11, comprising an electronic component group having a plurality of electronic components,
  wherein the electronic component group has a management circuit configuring at least some of the plurality of electronic components and configured to manage the light-emitting element based on the intensity of the fluorescence detected by the photodetection element.

13. The ultraviolet-emitting device according to claim 12, wherein at least one electronic component of the plurality of electronic components is disposed on an opposite side of a placement side of the light-emitting element with respect to the board.

14. The ultraviolet-emitting device according to claim 12, wherein the management circuit comprises:
  a setting unit configured to set a target value for causing the light-emitting element to emit light with a desired emission intensity; and
  an automatic power controller configured to maintain the light-emitting element at the desired emission intensity.

15. The ultraviolet-emitting device according to claim 14, wherein the setting unit comprises:
  an amplifier configured to amplify a voltage based on a detection signal obtained by the photodetection element;
  a bias adjuster configured to adjust a DC bias of the voltage output from the amplifier;
  an offset adjuster configured to adjust an offset voltage included in the voltage output from the amplifier; and
  an addition unit configured to sum the voltage output from the amplifier, the voltage output from the bias adjuster, and the voltage output from the offset adjuster.

16. The ultraviolet-emitting device according to claim 14, wherein the management circuit comprises a driver configured to drive the light-emitting element, and
  the automatic power controller comprises:
  an analog-to-digital converter configured to convert an analog signal output from the setting unit into a digital signal;
  a determination unit configured to determine whether the light-emitting element maintains the desired emission intensity based on the digital signal converted by the analog-to-digital converter; and
  a generator configured to generate a control signal for controlling the driver based on an instruction from the determination unit.

17. The ultraviolet-emitting device according to claim 16, further comprising a temperature detector configured to detect a temperature of the light-emitting element,
  wherein the automatic power controller controls the driver based on the temperature detected by the temperature detector.

18. The ultraviolet-emitting device according to claim 14, wherein the management circuit stops an operation of the light-emitting element when the management circuit determines that external light has entered the accommodation space while the light-emitting element is operated in a state in which the object to be sterilized is ready to be sterilized.

19. The ultraviolet-emitting device according to claim 11, wherein the fluorescent glass element is formed in a pillar shape and has, at one end, an inclined surface lower in a direction away from the light-emitting element.

20. The ultraviolet-emitting device according to claim 11, wherein the fluorescent glass element is formed in a shape having a spherical surface.

* * * * *